United States Patent
Lim et al.

(10) Patent No.: US 10,995,186 B2
(45) Date of Patent: May 4, 2021

(54) LIGHT-ACTIVATED PREPARATION OF HYDROGELS

(71) Applicant: Otago Innovation Limited, Dunedin (NZ)

(72) Inventors: Shen Khoon Lim, Christchurch (NZ); Timothy Bryan Francis Woodfield, Christchurch (NZ); Gabriella Christina Johanna Lindberg, Christchurch (NZ)

(73) Assignee: Otago Innovation Limited, Dunedin (NZ)

( * ) Notice: Subject to any disclaimer, the term of this patent is extended or adjusted under 35 U.S.C. 154(b) by 0 days.

(21) Appl. No.: 15/781,246

(22) PCT Filed: Dec. 2, 2016

(86) PCT No.: PCT/NZ2016/050192
§ 371 (c)(1),
(2) Date: Jun. 4, 2018

(87) PCT Pub. No.: WO2017/095240
PCT Pub. Date: Jun. 8, 2017

(65) Prior Publication Data
US 2018/0355127 A1    Dec. 13, 2018

Related U.S. Application Data

(60) Provisional application No. 62/380,189, filed on Aug. 26, 2016, provisional application No. 62/262,245, filed on Dec. 2, 2015.

(51) Int. Cl.
| | |
|---|---|
| C08J 3/28 | (2006.01) |
| A61L 27/52 | (2006.01) |
| A61L 27/38 | (2006.01) |
| A61L 27/54 | (2006.01) |
| C08J 3/075 | (2006.01) |
| C08L 5/10 | (2006.01) |
| A61L 27/56 | (2006.01) |
| C08B 37/00 | (2006.01) |
| C08K 3/30 | (2006.01) |
| C08K 5/56 | (2006.01) |

(52) U.S. Cl.
CPC ............. *C08J 3/28* (2013.01); *A61L 27/38* (2013.01); *A61L 27/52* (2013.01); *A61L 27/54* (2013.01); *A61L 27/56* (2013.01); *C08B 37/0075* (2013.01); *C08J 3/075* (2013.01); *C08K 3/30* (2013.01); *C08K 5/56* (2013.01); *C08L 5/10* (2013.01); *A61L 2300/102* (2013.01); *A61L 2300/414* (2013.01); *A61L 2400/12* (2013.01); *A61L 2430/06* (2013.01); *C08J 2305/10* (2013.01); *C08J 2329/04* (2013.01); *C08J 2333/12* (2013.01); *C08J 2333/26* (2013.01); *C08J 2367/04* (2013.01); *C08J 2371/02* (2013.01); *C08J 2389/00* (2013.01); *C08K 2003/3054* (2013.01)

(58) Field of Classification Search
CPC . C08J 3/28; C08J 3/075; C08J 2371/02; C08J 2367/04; C08J 2333/26; C08J 2333/12; C08J 2329/04; C08J 2305/10; C08J 2389/00; C08B 37/0075; C08L 5/10; C08K 5/56; C08K 3/30; C08K 2003/3054; A61L 27/54; A61L 27/38; A61L 27/52; A61L 27/56; A61L 2430/06; A61L 2300/414; A61L 2400/12; A61L 2300/102; C08F 2/50
See application file for complete search history.

(56) References Cited

U.S. PATENT DOCUMENTS

2011/0190813 A1    8/2011    Brownlee et al.
2014/0377326 A1    12/2014    Niu et al.

FOREIGN PATENT DOCUMENTS

WO    WO 2003/009014    1/2003

OTHER PUBLICATIONS

Benton Photocrosslinking to Synthesize Porous Hydrogels Tissue Engfineering, p. 3221 (Year: 2009).*
International Search Report for PCT/NZ2016/050192, dated Dec. 2, 2016.
Bjork, J. W. et al., "Ruthenium-catalyzed photo cross-linking of fibrin-based engineered tissue." Biomaterials, 2011, vol. 32, issue 10, pp. 2479-2488.
Kamoun, E. A. et al., "HES-HEMA nanocomposite polymer hydrogels: swelling behavior and characterization." J Polym Res, 2012, vol. 19, article 9851.
Lin, C-C et al., " Thiol-Norbornene Photoclick Hydrogels for Tissue Engineering Applications." J. Appl. Polym. Sci., 2015, vol. 132, iss. 7-8, article 41563.
Nguyen, K. T. et al., "Photopolymerizable hydrogels for tissue engineering applications." Biomaterials, 2002, vol. 23, pp. 4307-4314.
Rivarola, C. R. et al., "A visible light photoinitiator system to produce acrylamide based smart hydrogels: $Ru(bpy)_3^{+2}$ as photopolymerization initiator and molecular probe of hydrogel microenvironments." Polymer, 2009, vol. 50, pp. 3145-3152.
Zhou, D. et al., "Visible light-curable polymers for biomedical applications." Science China Chemistry, 2014, vol. 57, pp. 510-521.

* cited by examiner

Primary Examiner — Matthew P Coughlin
Assistant Examiner — Thurman Wheeler
(74) Attorney, Agent, or Firm — Barnes & Thornburg LLP; Ryan L. Marshall

(57) ABSTRACT

A method for preparing a hydrogel comprising mixing a solution of a polymer with a photoinitiator, where the polymer comprises multiple subunits each having a non-aromatic unsaturated functional group, and irradiating the mixture with visible light to produce the hydrogel.

18 Claims, 19 Drawing Sheets

LIGHT-ACTIVATED PREPARATION OF HYDROGELS

CROSS REFERENCE TO RELATED APPLICATIONS

This application is a 371 national phase of PCT/NZ2016/050192, filed Dec. 2, 2016, and claims the benefit under 35 U.S.C. § 119(e) of U.S. Provisional Application No. 62/380,189, filed Aug. 26, 2016, and of U.S. Provisional Application No. 62/262,245, filed Dec. 2, 2015, the disclosures of which are incorporated, in their entirety, by this reference.

TECHNICAL FIELD

The invention relates to the preparation of a hydrogel by crosslinking of polymer molecules using visible light photoinitiation. In particular, the invention relates to a method for preparing a hydrogel by mixing a polymer with a photoinitiator and irradiating the mixture with visible light. Hydrogels produced in this way have a variety of uses including tissue engineering uses.

BACKGROUND OF THE INVENTION

Articular cartilage is found at the surface of the articular joint and functions to facilitate the transmission of loads. However, chronic disease such as arthritis leads to degeneration and erosion of the cartilage, causing movement instability as well as significant impairment to the quality of life. Recent statistics show that 52.5 million adults in the USA have arthritis and this figure is projected to increase to 67 million by year 2030. As cartilage is an avascular tissue, it has limited capacity for intrinsic healing and repair. Although therapies such as autologous chondrocyte implantation and microfracture have been implemented in clinics, these treatments are only able to provide symptomatic relief until the need for surgical joint replacement. Therefore, new strategies to repair or replace the damaged cartilage are being sought.

In recent years, tissue engineering approaches which combine cells, signalling factors and scaffolds, have emerged as promising treatments for arthritis. These scaffolds are mostly hydrogels, which are highly hydrated polymeric networks and have previously been shown to have structural similarity to native extracellular matrix. Their high water content allows good permeability and diffusion of nutrients and oxygen to the encapsulated cells, as well as waste products released from the cells to the environment. These hydrogels can be fabricated from synthetic polymers such as poly(vinyl alcohol) (PVA), poly(ethylene glycol) (PEG) or from biological polymers such as alginate, hyaluronan, collagen and gelatin. Among all these hydrogels, gelatin has emerged as a potential material for cartilage repair. It is water soluble with low immunogenicity but most importantly, being a product of collagen hydrolysis, it also retains many of the native molecular epitopes in collagen that are important for cell signalling and maintenance of chondrocyte phenotype.

In particular, gelatin hydrogels fabricated by photo-polymerisation are especially attractive as spatial and temporal control over the polymerisation process is possible, and the process can be performed at room or physiological temperature, with fast curing rates and minimal heat generation. This photo-polymerisation process often requires grafting gelatin with functional moieties such as methacryloyl groups. Depending on the degree of methacryloylation and the macromer concentration, the physical properties (crosslinking density, swelling and stiffness) of the gelatin-methacryloyl (Gel-MA) hydrogels can be tailored, which makes this material a versatile platform for various tissue engineering applications. To date, the most commonly used photo-initiator for crosslinking Gel-MA is 1-[4-(2-hydroxyethoxy)-phenyl]-2-hydroxy-2-methyl-1-propane-1-one, which is also known as Irgacure2959 (12959). When exposed to ultraviolet (UV) light, the 12959 molecules absorb photons of light and dissociate into radicals, which then propagate through the methacryloyl groups, forming covalent kinetic chains to hold the polymer chains together.

However, one major drawback of using this system is that 12959 requires UV light for photo-excitation, which can potentially damage cellular DNA. Previous studies have shown that both UVA (320-400 nm) and UVB (290-320 nm) radiation induce chromosomal as well as genetic instability in mammalian cells. UV light can also produce reactive oxygen species (ROS) which can cause oxidative damage to the DNA. Therefore, photo-polymerisation systems using visible light (400-700 nm), which is less phototoxic to cells, are more favourable for tissue engineering applications.

A number of visible light initiating systems such as camphorquinone, fluorescein, riboflavin and rose bengal have been examined to fabricate cell-laden hydrogels. However, these initiators have poor water solubility and limited photo-reactivity or cytotoxicity. A recently synthesised photo-initiator, lithium phenyl-2,4,6-trimethylbenzoylphosphinate (LAP), which absorbs at 405 nm, has good photo-reactivity as well as cyto-compatibility.

However, LAP requires a complex synthesis route and is not yet commercially available. In contrast, another new emerging visible light initiating system consisting of commercially available initiators, a ruthenium (Ru) based transition metal complex and sodium persulfate (SPS), has shown potential for tissue engineering applications. This Ru/SPS system has been used to crosslink polymers with phenol moieties, where the resultant hydrogels have been applied as tissue sealants or matrices to encapsulate fibroblasts and neural cells. When irradiated with visible light, $Ru^{2+}$ photo-excites into $Ru^{3+}$ by donating electrons to SPS. The photo-excited $Ru^{3+}$ then reacts with phenol groups on the polymers forming covalent crosslinks. After accepting electrons, SPS dissociates into sulfate anions and sulfate radicals. These sulfate radicals can propagate through the methacryloyl groups causing covalent crosslinking. However, a significant disadvantage of crosslinking via phenol groups is that crosslinking efficiency is low. Consequently, the amount of light energy required to generate sufficient crosslinking can be very high. Further, hydrogels formed using this photoinitiation/crosslinking system tend to have limited mechanical characteristics. They are often not tailorable to different applications due to poor physico-chemical properties.

One problem associated with the preparation of many hydrogels, including Gel-MA hydrogels, is the effect of oxygen inhibition. In the case of some photo-polymerisation systems, e.g. the use of UV light (320-365 nm) and the photo-initiator 12959, any oxygen present is able to quench the radicals required for crosslinking. This results in incomplete or insufficient formation of crosslinks and therefore the inability of the construct to maintain its shape. This is especially important for the use of hydrogels as bio-inks in computer-aided biofabrication techniques for building 3-dimensional constructs or scaffolds of biomaterials. A hydrogel preparation system that exhibits low levels of oxygen inhibition of hydrogel formation is advantageous.

It is therefore an object of the invention to overcome or ameliorate one or more of the above mentioned disadvantages or problems by providing a hydrogel that can be prepared by irradiation of a polymer using visible light or to at least provide a useful alternative to known hydrogel formation systems.

SUMMARY OF THE INVENTION

In a first aspect of the invention there is provided a method for preparing a hydrogel comprising the steps:
  (i) mixing a solution of a polymer with a photoinitiator, where the polymer comprises multiple subunits each having a non-aromatic unsaturated functional group; and
  (ii) irradiating the mixture with visible light to produce the hydrogel.

In a second aspect of the invention there is provided a use of a hydrogel prepared according to the first aspect of the invention for manufacture or repair of tissue, such as cartilage, in a human or non-human animal.

In a third aspect of the invention there is provided a use of a hydrogel prepared according to the first aspect of the invention as a bio-ink or bio-resin.

BRIEF DESCRIPTION OF THE FIGURES

FIG. 16 shows Gel-MA cell-laden hydrogel beads fabricated using a micro-fluidic approach.

DETAILED DESCRIPTION

Figure 1:
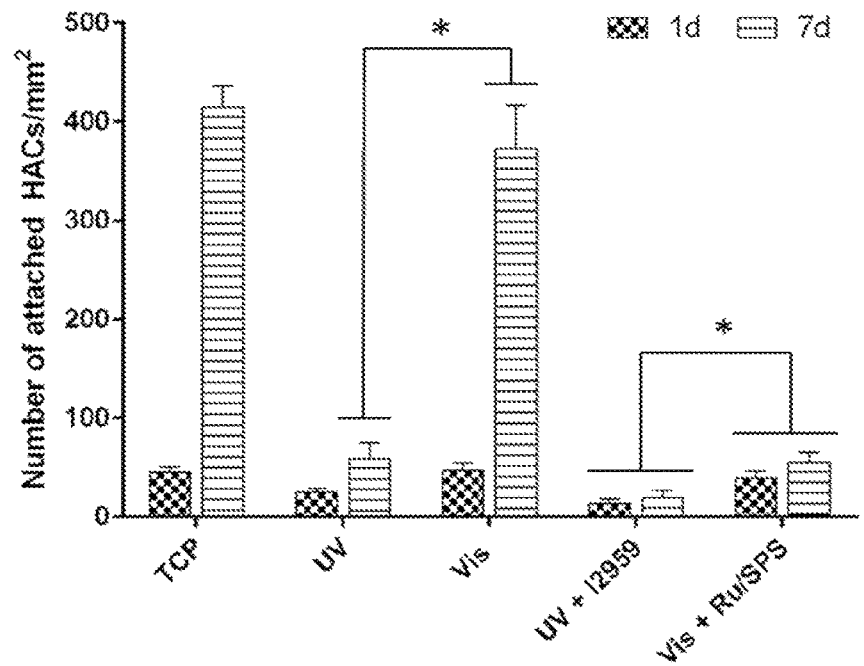
FIG. 1 shows an evaluation of photo-toxicity (UV vs visible light) and radical toxicity (UV+I2959 vs visible light+Ru/SPS) using HACs cultured on 2D surfaces.

The invention relates generally to a method for preparing a hydrogel using visible light, rather than UV light, to initiate crosslinking of polymer chains to form a hydrogel. Because UV light is damaging to biological cells, the preparation of a hydrogel using visible light is advantageous for applications where it is beneficial, or even critical, to avoid the damage of cells. Such applications include animal (especially human) tissue engineering procedures. The crosslinking of the polymer chains is via unsaturated functional groups of the polymer. Importantly, the unsaturated functional groups are non-aromatic. The inventors have found that problems associated with the crosslinking of polymers having aromatic functional groups, such as phenol groups, can be avoided. They determined that non-aromatic functional groups, such as methacryloyl, crosslink via photoinitiation with much greater efficiency and lead to the formation of hydrogels with more desirable physico-chemical properties. This also enables manufacturing process conditions to be better controlled therefore providing hydrogels and bio-inks that are tailored for specific uses or applications.

The term "gel" means a substantially dilute cross-linked system which exhibits no flow when in the steady-state.

The term "hydrogel" means a gel comprising a network of polymer chains that are hydrophilic. Hydrogels are highly absorbent (they can contain over 90% water) natural or synthetic polymeric networks.

The term "polymer" means a synthetic or natural macromolecule comprising many repeated subunits.

The term "polymer chain" means a length of polymer comprising multiple subunits linked together in the form of a chain.

The term "gelatin" means any mixture of peptides and proteins produced by the partial hydrolysis of collagen. Collagen is the main structural protein in the extracellular space in the skin, bones and connective tissues of animals such as cattle, chicken, pigs, horses and fish.

The term "heparin" means a carbohydrate of the glycosaminoglycan family and consists of a variably sulfated repeating disaccharide unit. The most common disaccharide unit is composed of a 2-O-sulfated iduronic acid and 6-O-sulfated, N-sulfated glucosamine.

The term "photoinitiator" means a compound or combination of two or more compounds that produces free radicals when exposed to light.

The term "functional group" means a group of atoms or bonds within a molecule that are responsible for chemical reactions of that molecule.

The term "unsaturated functional group" means a functional group having at least one double bond or triple bond.

The term "aromatic" means relating to or denoting an organic compound or functional group containing a planar unsaturated ring of atoms which is stabilised by interaction of delocalized pi electrons between the atoms forming the ring, e.g. benzene and its derivatives.

The term "non-aromatic unsaturated functional group" means a functional group having at least one double bond or triple bond and is not an aromatic functional group.

The term "bio-ink" means a hydrogel that can be 3D-printed, 3D-plotted or fabricated into a particular shape or construct, and is cell cytocompatible. The hydrogel may or may not incorporate living cells and/or growth factors.

The term "bio-resin" means a hydrogel that can be 3D-printed or fabricated into a particular shape or construct using laser or light projection-based light stereolithography, or similar lithographic techniques, and is cell cytocompatible. The hydrogel may or may not incorporate living cells and/or growth factors.

The method of the invention relates to the preparation of a hydrogel comprising the steps:
  (i) mixing a solution of a polymer with a photoinitiator, where the polymer comprises multiple subunits each having a non-aromatic unsaturated functional group; and
  (ii) irradiating the mixture with visible light to produce the hydrogel.

In some embodiments of the invention the unsaturated functional group comprises a double bond. In other embodiments the unsaturated functional group is a triple bond. Examples include methacrylate, acrylate, methacrylamide, acrylamide, norbornene, propiolate, and allyl groups.

In some embodiments of the invention the hydrogel forms by cross-linking of unsaturated functional groups by a chain-growth polymerisation process. In other embodiments the hydrogel forms by cross-linking of unsaturated functional groups by a step-growth polymerisation process. The step-growth polymerisation process preferably comprises a reaction between one or more unsaturated functional groups of one polymer chain and thiolated functional groups of another polymer chain.

The photoinitiator may be any suitable compound or mixture of compounds that produces radical species upon irradiation with visible light to enable crosslinking of polymer chains. One type of photoinitiator is combination of a ruthenium(II) compound and sodium persulfate, ammonium persulfate or potassium persulfate. One example of the ruthenium(II) compound is tris(2,2-bipyridyl)-dichlororuthenium(II) hexahydrate.

In some embodiments of the invention the polymer is a synthetic polymer. Examples include polyvinyl alcohol (PVA), polyethylene glycol (PEG), poly(2-hydroxyethyl methacrylate) (pHEMA), poly(acrylamide), poly(methacrylamide), poly(methyl methacrylate) (PMMA), poly(lactide-co-trimethylene carbonate) (PTMC), polyfumarate, poly(lactic acid) (PLA), polycaprolactone (PCL) and poly(N-vinyl-2-pyrrolidone).

In other embodiments the polymer is a natural polymer. Examples include alginate, hyaluronan, heparin, silk fibroin, silk sericin, methylcellulose, gellan gum, chondroitin sulfate, chitosan, fibrinogen, collagen, gelatin, vascular endothelial growth factor (VEGF), bone morphogenic protein (BMP), epidermal growth factor (EGF), brain derived neurotrophic factor (BDNF) and transforming growth factor (TGF).

The visible light used in the method of the invention may have a wavelength in any range suitable for enabling cross-linking of the polymer. A preferred range is 400-450 nm.

In certain embodiments of the invention, the hydrogel is a gelatin-methacryloyl hydrogel, a heparin-methacryloyl hydrogel, a poly(vinyl alcohol)-methacryloyl hydrogel, a gelatin-allyloyl hydrogel, or a gelatin-norbornenyl hydrogel.

One method used to prepare the gelatin-methacryloyl hydrogel comprises the steps:
 (i) contacting an aqueous solution of gelatin with methacrylic anhydride to produce gelatin-methacryloyl;
 (ii) mixing the gelatin-methacryloyl with a ruthenium(II) compound and sodium persulfate; and
 (iii) irradiating the mixture with visible light to produce the hydrogel.

The intensity of the light used may be in the range 10-100 mW/cm$^2$, for example 10, 20, 30, 40 or 50 mW/cm$^2$, preferably 30 mW/cm$^2$, or any other intensity in that range.

The ratio of the ruthenium(II) compound to sodium persulfate may be any suitable ratio (for example 1:2, 1:3, 1:4, 1:5, 1:6, 1:7, 1:8, 1:9, 1:10, 1:11, 1:12, 1:13, 1:14 or 1:15), but is preferably 1:10.

The light irradiation time may be any suitable time for enabling crosslinking of the polymer. In some embodiments of the invention, the irradiation time is 2-15 minutes (for example 2, 3, 4, 5, 6, 7, 8, 9, 10, 11, 12, 13, 14 or 15 minutes).

In some embodiments of the invention the hydrogel comprises encapsulated biological cells and/or cellular spheroids.

In some embodiments of the invention the hydrogel comprises one or more encapsulated growth factors, e.g. VEGF, BMP2, EGF, BDNF or TGF-β.

In some embodiments of the invention the hydrogel comprises nanoparticles, for example nanoparticles comprising magnesium or strontium compounds.

In some embodiments of the invention inhibition by oxygen of the formation of the hydrogel in the irradiation step is reduced compared to irradiation of a polymer and a photo-initiator using UV light.

The hydrogel prepared according to the invention may be used for a variety of applications including, but not limited to, the manufacture or repair of tissue (e.g. cartilage) in a human or non-human animal, and the use as a bio-ink or bio-resin for the 3-dimensional biofabrication or 3-dimensional bioprinting of a biological construct. The biological construct may be any animal tissue or organ, or part thereof, that is able to be manufactured using a biofabrication or bioprinting technique, e.g. a scaffold containing cells which may be porous or non-porous.

The invention is described below in detail with reference to gelatin-methacryloyl (Gel-MA) hydrogels, but it will be appreciated that various similar hydrogels will function in the same or similar way.

Example 1 describes how to prepare a Gel-MA hydrogel. Examples 2 to 8 compare a visible light system with a UV photo-polymerisation system. The photo-toxicity and radical toxicity of the visible light system was compared to the conventional UV+I2959 system, firstly using a 2D model consisting of human articular chondrocytes (HAC) cultured on tissue culture plastic (TCP). As shown in FIG. 1, significant cell proliferation was observed from day 1 (50 HACs/mm$^2$) to day 7 (400 HACs/mm$^2$) for the TCP control. However, exposing these cells to 15 minutes of UV light significantly perturbed the cell growth, where only 80 HACs/mm$^2$ were obtained after day 7. On the other hand, irradiating the cells with 15 minutes of visible light did not affect the cell growth, where the total number of attached cells at day 7 was not significantly different to the TCP control. This result indicates that UV light is more phototoxic to the cells, which is in accordance with previous studies. Upon introduction into both systems of the initiators, significant reduction in cell proliferation was observed. Because free radicals are generated when the cells are irradiated with light in the presence of the initiators, this observation shows that these radicals are cytotoxic to the cells, and can impair cell proliferation. Nevertheless, it was also observed that Vis+Ru/SPS samples had significantly higher number of cells attached (60 HACs/mm$^2$) after 7 days compared to the UV+I2959 samples (20 HACs/mm$^2$), highlighting better cell tolerability of the visible light system.

Live-dead stains were performed according to Example 5 on the samples after 7 days of incubation post treatment. The morphology of the cells attached to the surfaces clearly showed that for the TCP control, cells were elongated and remained spindle-shaped which is normally seen for chondrocytes in expansion. Although irradiating the cells with UV light significantly reduced the number of cells attached, the elongated and spindle-shape morphology remained. However, when the UV light was combined with the initiator I2959, a change in morphology was seen, where the cells became rounded, indicating cytoskeletal impairment. In comparison, no obvious difference was observed between the TCP control and cells irradiated with visible light. Although a significant decrease in cell number was observed in the Vis+Ru/SPS samples, the cells still remained stretched and spindle-shaped.

Figure 2:
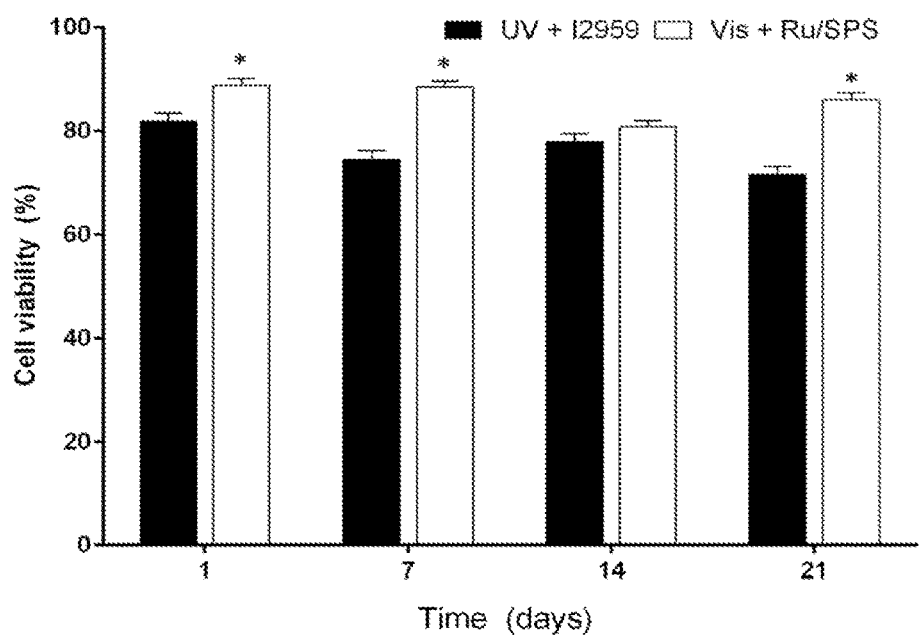
FIG. 2 shows the cell viability of HACs encapsulated in Gel-MA hydrogels fabricated using UV+I2959 or Vis+Ru/SPS at 1, 7, 14 and 21 days. *Denotes statistical significance (p<0.05) compared to UV+I2959 at respective time points.

As the objective is to utilise the Gel-MA gels for 3D cell delivery, HACs were encapsulated into the Gel-MA hydrogels according to Example 4. Live-dead assays were performed to evaluate the viability of the cells over 3 weeks. The results are shown in FIG. 2. After 1 day post polymerisation, it could be seen that the Vis+Ru/SPS system had significantly higher cell viability (90%) than the UV+I2959 system (80%). The cells encapsulated using the UV+I2959 system showed a decrease in viability where only 70% remained alive after 21 days. On the other hand, the Vis+Ru/SPS samples showed consistent viability above 80% over the whole 21 days. This highlights the lower cytotoxic effect of the visible light system compared to the UV crosslinking system.

Images for the live-dead assay of samples prepared according to Example 4 showed that the cell-laden gels fabricated using the UV+I2959 system had more dead cells compared to the Vis+Ru/SPS system for all time points examined. This confirmed the results obtained in the cell viability study. In a 3D environment, chondrocytes are meant to exhibit a rounded morphology as an indication of their native phenotype. After 21 days, the encapsulated cells were not only homogenously distributed, but also remained rounded.

Figure 3:
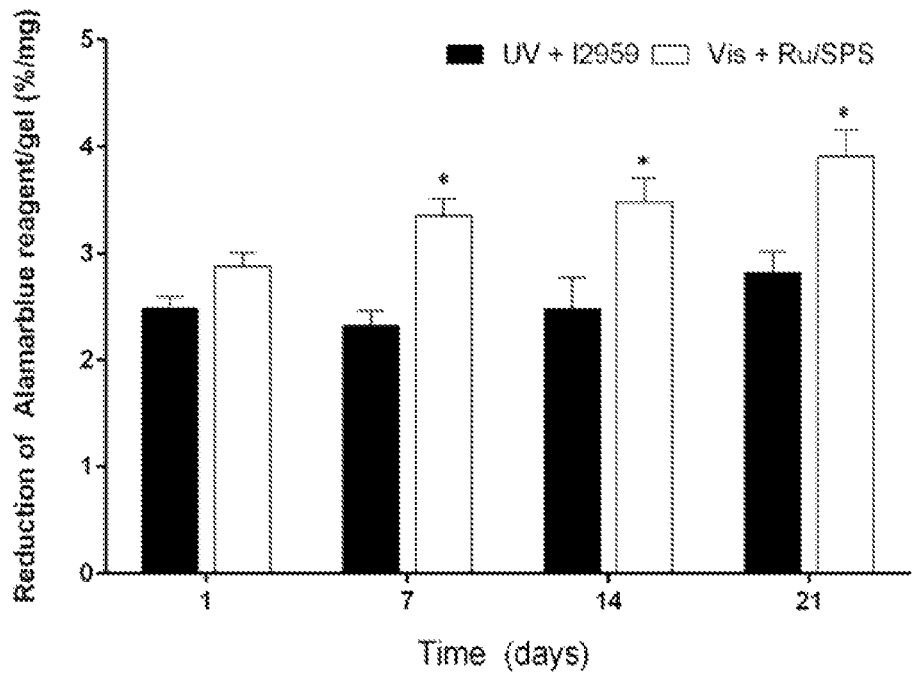
FIG. 3 shows the metabolic activity of cells encapsulated in Gel-MA hydrogels fabricated using UV+I2959 or Vis+Ru/SPS at 1, 7, 14 and 21 days. *Denotes statistical significance (p<0.05) compared to UV+I2959 at respective time points.

Furthermore, the metabolic activities of the samples were examined according to Example 6 in order to evaluate the functionality of the encapsulated cells. It was clearly seen that the Vis+Ru/SPS samples had a significantly higher metabolic activity at 7, 14 and 21 days compared to UV+I2959. The results are shown in FIG. 3. This example shows that cells encapsulated using the visible light system not only have better viability but also are more functional as indicated by the higher metabolic activity post encapsulation.

Figure 4:
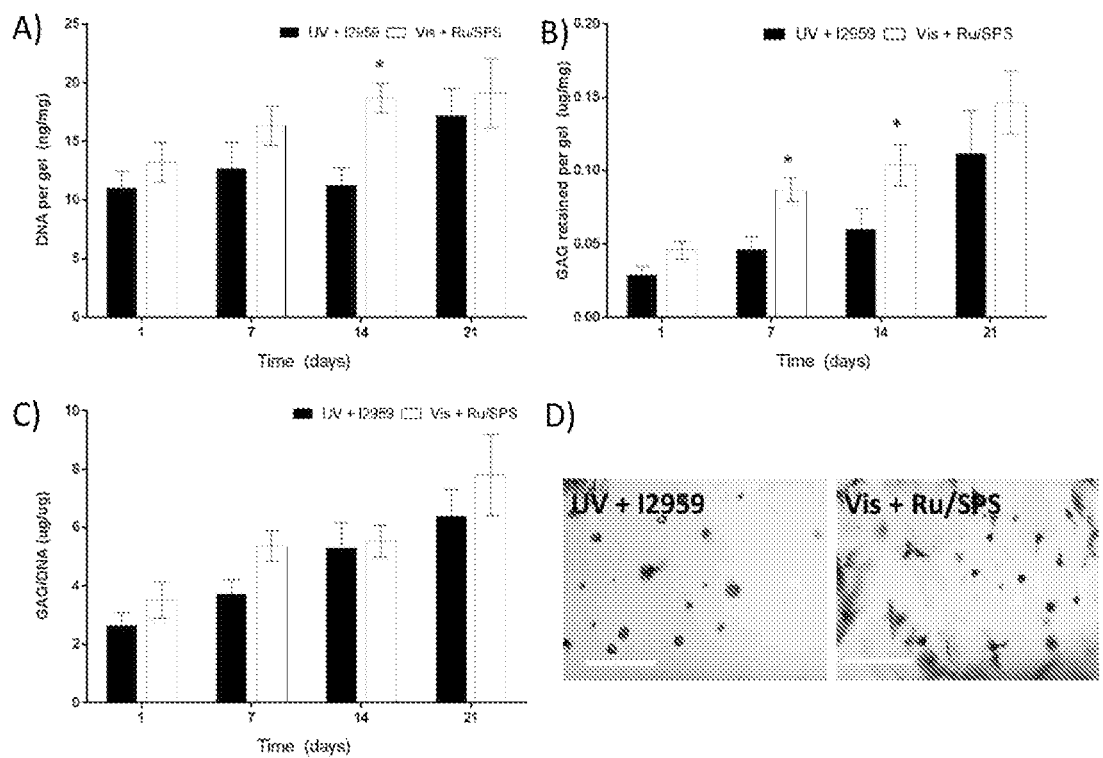
FIG. 4 shows the chondrogenic differentiation of HAC encapsulated in Gel-MA hydrogels using UV+I2959 or Vis+Ru/SPS: A) DNA per gel; B) GAG retained per gel; C) GAG/DNA and D) Histology of cell-laden Gel-MA hydrogels after 21 days, safranin-O staining indicating GAG production (red) (Scale bar=100 μm).

The chondrogenic differentiation of the cells post encapsulation was examined according to Example 7 to assess their potential as gels for cartilage engineering. It was found that after 21 days in culture, there were no significant differences between the UV+I2959 and Vis+Ru/SPS samples in terms of the total amount of DNA in the gels (FIG. 4A). However, in terms of tissue formation, the total amount of GAG accumulated in the constructs was significantly higher in the Vis+Ru/SPS samples at time points 7 and 14 days (FIG. 4B). At 21 days, although the GAG/gel in the Vis+Ru/SPS samples (0.15 µg/mg) was slightly higher than the UV+I2959 (0.1 µg/mg), there was no significant difference between these two samples. Nevertheless, this phenomenon indicates that the visible light system is supporting a faster rate of tissue formation. Histology images, prepared according to Example 8, show that the secreted GAGs were deposited in the pericellular region, where the visible light samples seem to have a larger GAG deposition area (FIG. 4D). On the other hand, there were no significant differences observed for the cells differentiation capability, which is given by the GAG/DNA at all time points (FIG. 4C).

Tissue engineering and regenerative medicine (TERM) strategies based on combining cells in tissue engineering scaffolds have been widely researched as potential solutions to replace or repair damaged and deceased tissues. These strategies have been employed to engineer various tissues such as bone, skin or cartilage. However, one challenge in TERM is the need for personalisation where different patients require dedicated personalised engineered tissue depending on the size and shape of the targeted tissue defect. Combining emerging biofabrication technologies with TERM, where materials are fabricated layer by layer from three dimensional data collected from patients, to engineer tissue constructs that are patient specific is a growing field.

Biofabrication techniques that enable precise control over the deposition of cells and biomaterials with the aid of a computer have shown great promise in fabricating constructs of complex and organised designs. There are several different types of biofabrication techniques such as laser-assisted printing, inkjet printing, micro-valve printing and extrusion printing. The latter two are generally more promising in building large constructs and more clinical relevance for tissue engineering. However, these techniques require specialised biomaterial platforms (bio-inks) which typically have specific rheological properties that allow the printing of constructs with good shape fidelity, as well as being cytocompatible to support the survival and function of cells. Hydrogels have shown promise as bio-inks due to their structural similarity to the native extracellular matrix. A number of hydrogels made from poly(ethylene glycol), poly(N-hydroxypropyl-methacrylamide lactate), alginate, hyaluronic acid, collagen, or gelatin, have been used as bio-inks.

Among all the different materials, gelatin hydrogels have shown potential as bio-inks for biofabrication of a variety of tissue types such as liver, skin, cancer models and cartilage. Gelatin is not only water soluble but also contains various peptide sequences that are known to support cell adhesion and proliferation, and are therefore highly favourable for tissue engineering approaches. However, gelatin has thermo-responsive rheological properties with a narrow but defined printing window for successful extrusion of fibres for building complex and organised structures. Therefore, the rheological behaviour of gelatin needs to be altered to allow better control of its extrudability in biofabrication applications. The inventors have found that collagen 1 can be incorporated into Gel-MA to give a hydrogel having improved rheological behaviour. The inventors have also found, importantly, that the effect of oxygen inhibition on biofabricated Gel-MA/collagen constructs is minimal.

Example 9 describes the preparation of Gel-MA/collagen hydrogels. Rheological measurements (Example 10) were conducted by maintaining the temperature at 20° C. while the shear rate was gradually increased from 1 to 1200/s. The Gel-MA+Collagen 1 macromer solutions had a significantly lower viscosity compared to a pure Gel-MA solution. The shear stress profiles as a function of shear rate showed that the addition of collagen 1 to Gel-MA significantly reduced the shear stress by at least half the magnitude. This indicates that the Gel-MA+Collagen 1 macromer solution has potential as a bio-ink because lower shear stress is exerted on the cells during the printing process.

Figure 6:
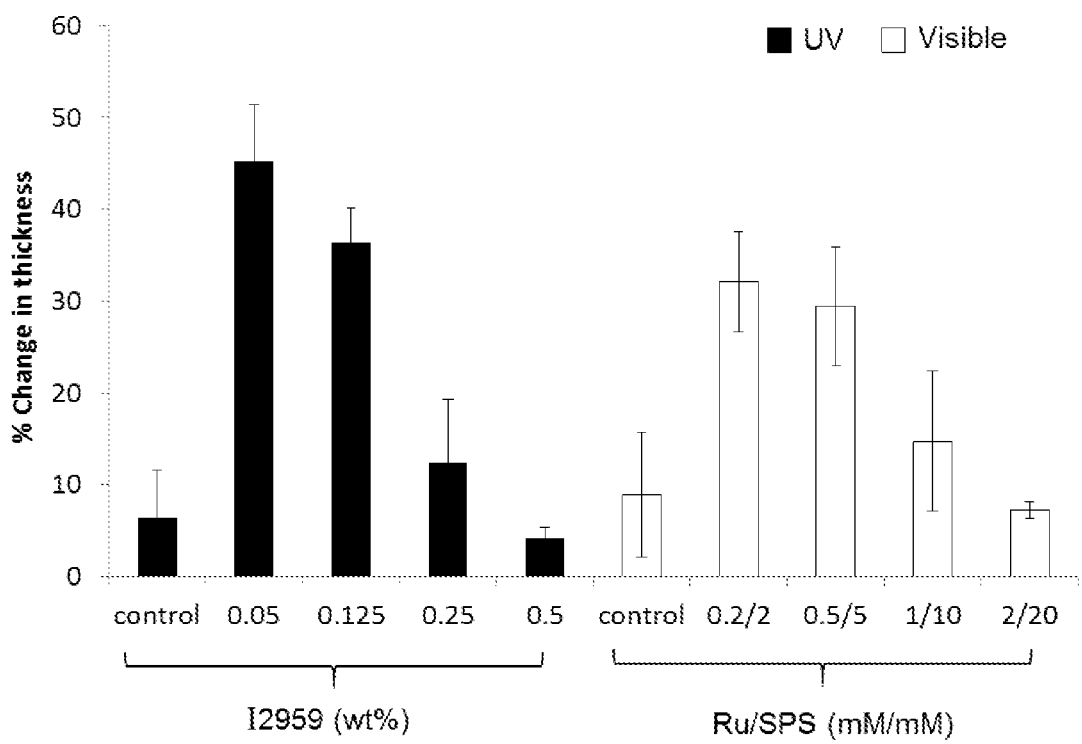
FIG. 6 shows the deformation of thickness of Gel-MA+Collagen 1 hydrogels at different initiator concentrations.

Example 11 relates to an investigation of the oxygen inhibition ability of Gel-MA/collagen hydrogels. Hydrogel discs were fabricated by casting Gel-MA+Collagen 1 macromer solution into disc moulds. The constructs were then irradiated in the presence of the photo-initiators and a light source (3 mW/cm$^2$), where the surfaces of the constructs were exposed to oxygen. The level of oxygen inhibition was evaluated by measuring the deformation of thickness of the gel constructs after equilibrium swelling. It was observed that for both the UV and visible light systems, low photo-initiator concentrations resulted in a significant deformation of thickness. Controls employed in this study were hydrogel discs fabricated without exposure to oxygen. The controls showed only <10% deformation of thickness. Increasing the photo-initiator concentrations did reduce the deformation of thickness in both systems, where samples made using 0.5 wt % I2959 and 2/20 Ru/SPS (mM) showed deformation of thickness comparable to the controls. The results are shown in FIG. 6.

Figure 7:
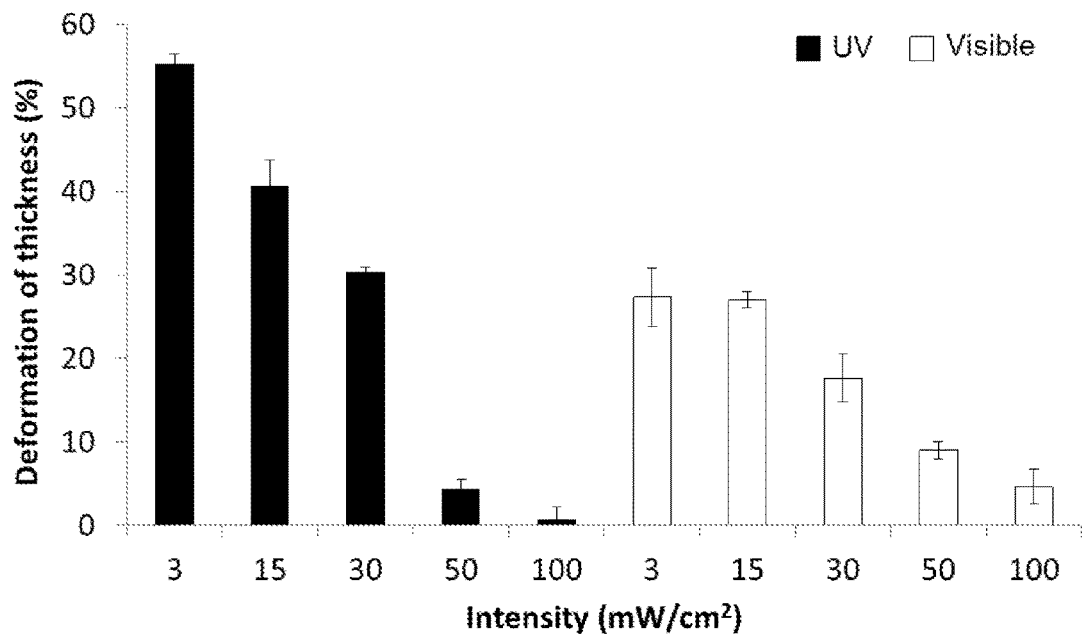
FIG. 7 shows the deformation of thickness of Gel-MA+Collagen 1 hydrogels at different light intensities.

Another approach to minimising oxygen inhibition is to increase the total exposure dosage by increasing the light intensity. The concentrations of photo-initiators utilised were kept at minimal (0.05 wt % I2959 and 0.2/2 Ru/SPS (mM) for the UV light and visible light systems respectively). It was found that increasing light intensity from 3 to 100 mW/cm$^2$ for both the UV and visible light systems successfully decreased oxygen inhibition (FIG. 7). Even at low intensity (3 mW/cm$^2$), the visible light system showed a reduction of thickness (~30%) significantly lower than the UV system (~55%).

Figure 8:
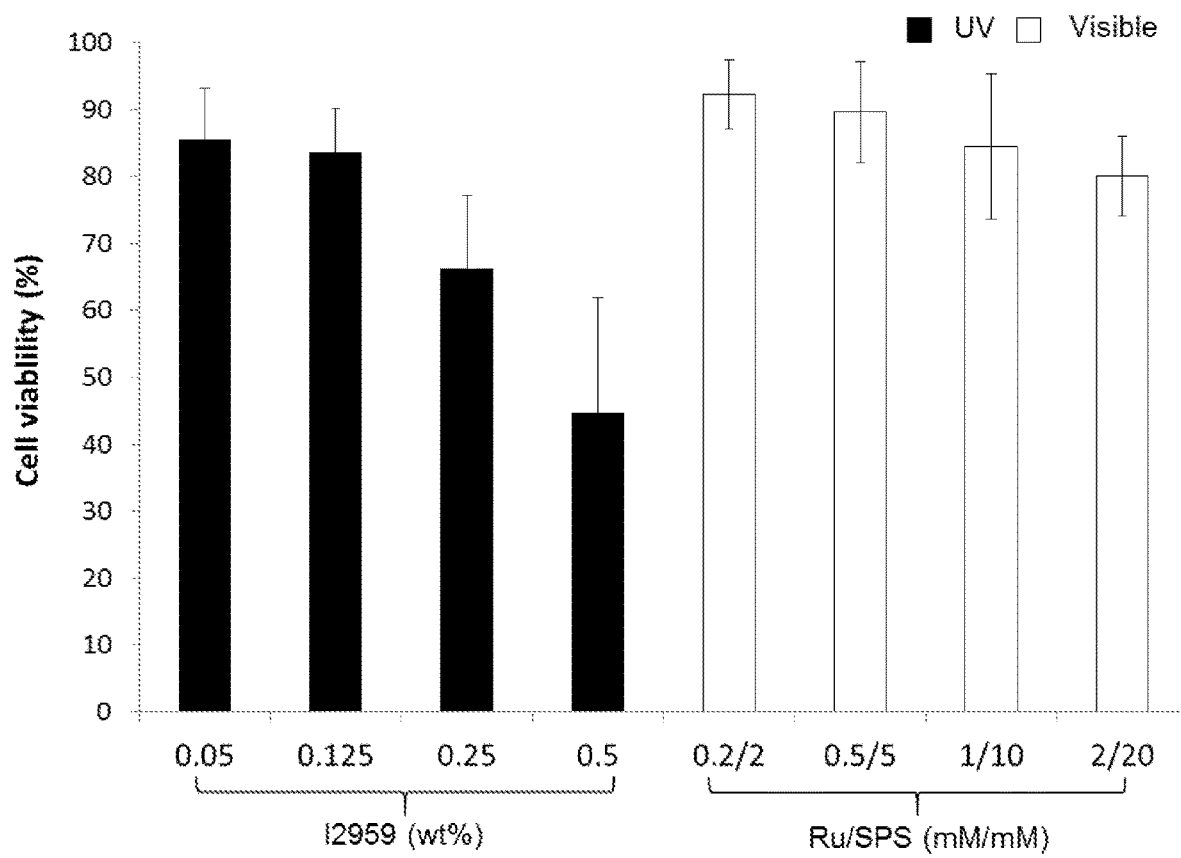
FIG. 8 shows the cell viability of MCF-7 in Gel-MA+Collagen 1 gels at different initiator concentrations.

In order to use bio-inks for the preparation of cell-laden constructs, it is important to know if the cells can survive photo-polymerisation conditions. It is known that high concentrations of photo-initiators and light intensity are generally toxic due to the generation of detrimental radicals and reactive oxygen species during the polymerisation process. Human breast adenocarcinoma (MCF-7) cells were encapsulated into these gels and their viability evaluated after 1 day (Example 12). It was shown that when light intensity is kept constant at 3 mW/cm$^2$, increasing the I2959 concentration significantly decreased the cell viability where 0.5 wt % I2959 resulted in 50% cell viability. However, surprisingly, an increase in the Ru/SPS concentration did not show a significantly detrimental effect on cell viability (FIG. 8).

Figure 9:
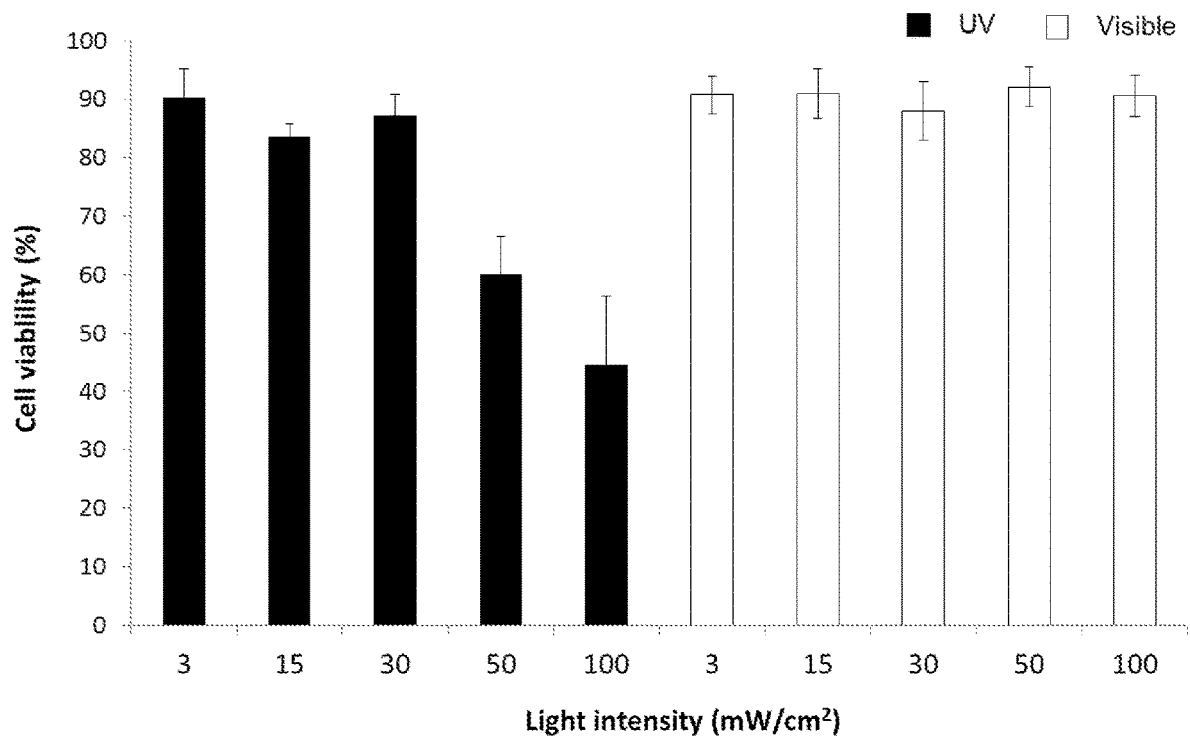
FIG. 9 shows the cell viability of MCF-7 in Gel-MA+Collagen 1 gels at different light intensities.

Moreover, Example 12 showed that the cell viability decreased with increasing UV intensity when the I2959 concentration was kept constant at 0.05 wt %. This is consistent with reports in the literature that UV light can damage the DNA and chromosomal stability of cells, killing them in the process. In contrast, the visible light system showed high cell viability (~90%) even at high light intensity (100 mW/cm$^2$), as shown in FIG. 9. This further highlights the potential of this visible light system for biofabrication of cell-laden constructs.

Example 13 describes an oxygen inhibition experiment involving 3D biofabricated constructs. The inventors found that at low UV light (3 mW/cm$^2$), the hydrogel construct was completely degraded after 1 day of equilibrium swelling, suggesting that a high level of oxygen inhibition occurred and the gels did not crosslink. Increasing the UV light intensity to 30 and 50 mW/cm$^2$ successfully produced constructs of good structural integrity after 1 day. In contrast, a hydrogel construct irradiated with 3 mW/cm$^2$ of visible light was still structurally intact after 1 day. At higher light intensities, it was also observed that the visible light system had lower level of reduction in fibre diameter, further indicating that the visible light system has lower level of oxygen inhibition, and is therefore a more suitable photo-polymerisation system for 3D biofabrication. Example 14 shows that cell-laden 3D printed constructs can be fabricated using this visible light system. The encapsulated cells showed high viability compared to using the UV light system.

The inventors have therefore shown for the first time that Gel-MA hydrogels can be prepared using a visible light initiated radical polymerisation system. The irradiation conditions were optimised and determined to be visible light intensity of 30 mW/cm$^2$, initiator concentration of 0.2/2 Ru/SPS (mM) and at least 3 minutes of exposure time. It should be noted that the Ru/SPS concentration required for Gel-MA is 10 times lower than the initiator combinations known for crosslinking other polymers through their phenol moieties. Without being bound by theory, the difference between Gel-MA and phenolated polymers may be due to differences in reactivity of different functional groups, as well as the different initiator components that are responsible for the crosslinking. During the photo-polymerisation process, Ru$^{2+}$ is photo-excited to Ru$^{3+}$ by donating electrons to SPS. For phenolated polymeric systems, the Ru$^{3+}$ is responsible for crosslink formation. However, in the method of the invention, the sulfate radicals, which are products from the dissociation of SPS, are responsible for reacting with the methacrylate groups on Gel-MA to form covalent crosslinks. The inventors have also shown that the minimum sol fraction (10-15%) and q (9-10) obtained are comparable to values obtained for Gel-MA gels fabricated using the UV+I2959 system. This indicates that the visible light system of the invention is capable of fabricating Gel-MA hydrogels of good physico-mechanical properties similar to the UV system.

The photo-toxicity of both the UV and visible light systems was evaluated using HACs culture on 2D surfaces. It was found that irradiating cells with UV significantly decreased cell proliferation. This result is consistent with earlier studies where UV has been shown to cause genomic instability to cells. In addition, UV is able to react with oxygen in the environment, forming reactive oxygen species (ROS) such as superoxide radicals ($O_2$.), hydroxyl radicals (OH.), singlet oxygen ($^1O_2$) and ozone ($O_3$), which can oxidise the lipid bilayer of cells. This lipid peroxidation may disrupt the cell membrane integrity and permeability, which can lead to up-regulation of tissue degrading enzymes and generation of toxic products. In contrast, visible light has been shown to have negligible photo-toxicity, and is therefore more clinically relevant. In terms of radical toxicity, it was found that even the Vis+Ru/SPS system resulted in significant impairment to cell proliferation. However, the UV+I2959 system has a greater cytotoxic effect on the cells, where even cell morphology was affected.

Encapsulated cells showed good cell viability (~80%) after 1 day for both systems. The inventors have shown that the Vis+Ru/SPS system produced cell-laden hydrogel constructs with viability of 90% after 1 day, which is significantly higher than previous studies. It should be noted that the cells in the visible light cross-linked gels had significantly higher metabolic activity than the UV gels. However, the chondrogenic differentiation study showed that although the GAG accumulation rate is faster in the visible light system, there was no significant difference in the re-differentiation capability of the cells (GAG/DNA). This may be due to the fact that the driving factor that dictates the re-differentiation capability of the cells is the 3D engineered matrix that is provided. As both the UV and visible light system result in Gel-MA gels that have comparable physico-mechanical properties, similar cellular functions and behaviour in these gels can be expected.

The potential benefit of the invention is that a system for hydrogel preparation using visible light is significantly advantageous in terms of clinical relevance and practicability for in vivo injectable hydrogel applications and minimally invasive surgery compared with the preparation of hydrogels using UV light. There is potential for this visible light+Ru/SPS system of the invention for the preparation of gelatin or Gel-MA gels for not only cartilage engineering, but also other tissue engineering applications including tissue glues or sealants, and those involving the use of bio-inks and 3D biofabrication or bioprinting of such bio-inks.

Figure 11:
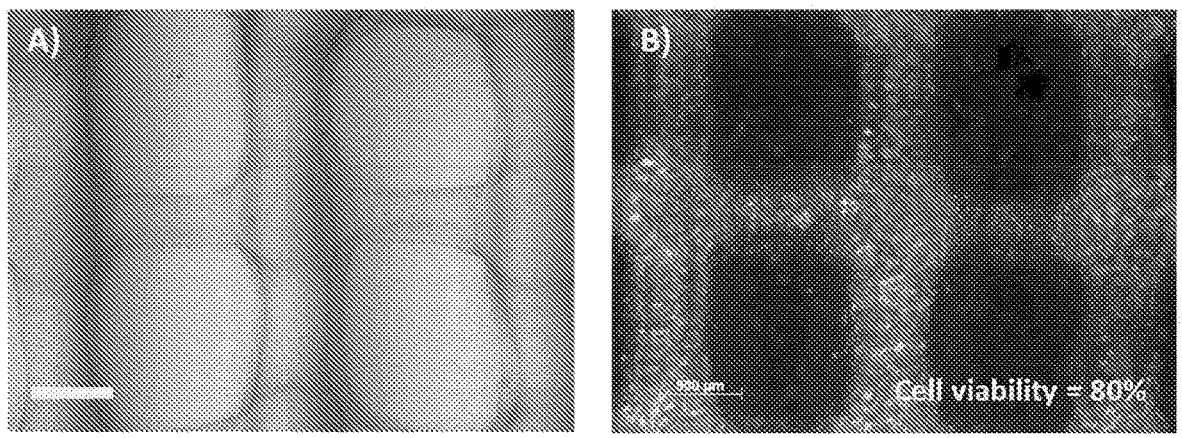
FIG. 11 shows 3D printed cell laden Gel-MA+Collagen 1 hydrogel constructs (Scale bar=500 μm).
Figure 12:
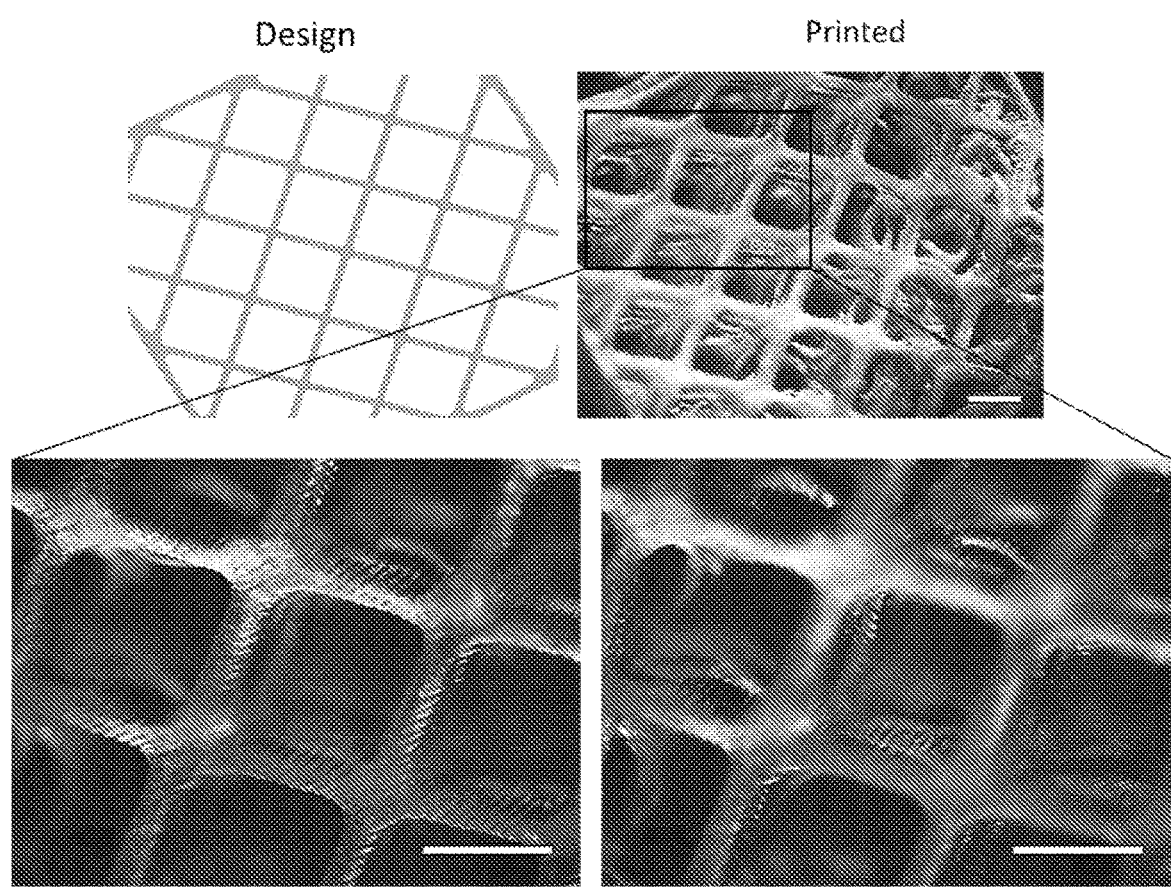
FIG. 12 shows porous layered PVA-MA hydrogel constructs fabricated using light projection stereolithography (Scale bar=500 μm).
Figure 13:
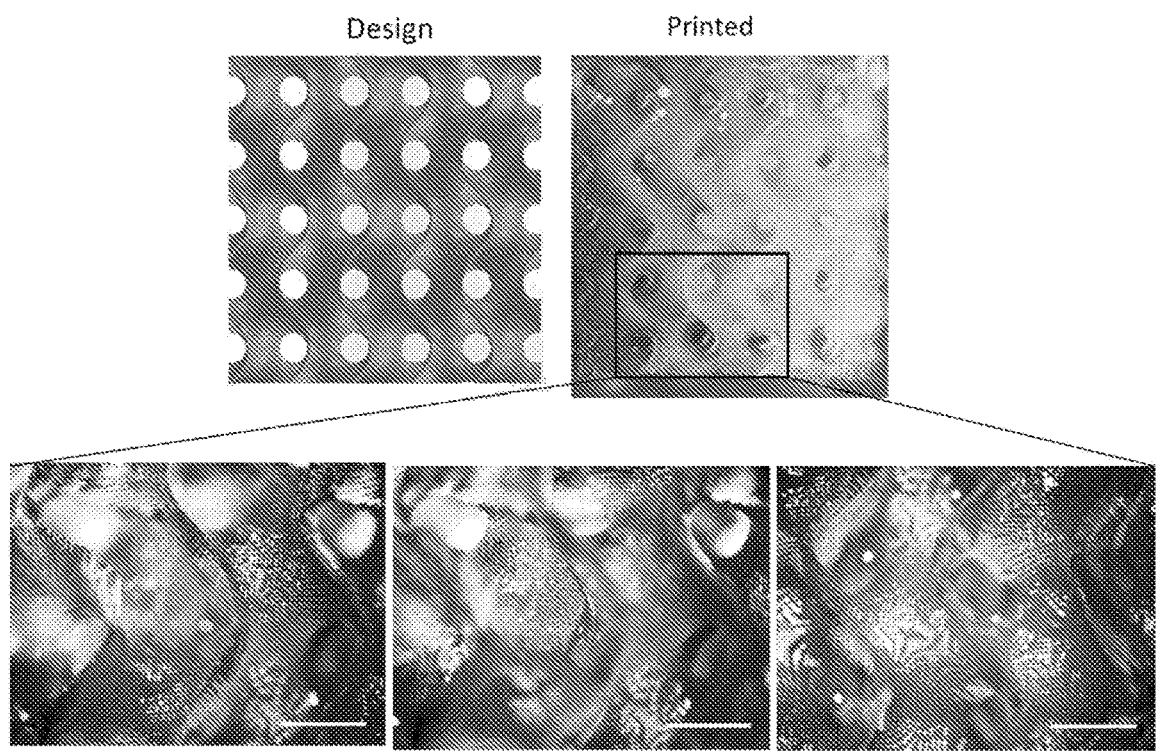
FIG. 13 shows porous PVA-MA gyroid hydrogel constructs fabricated using light projection stereolithography (Scale bar=500 μm).
Figure 14:
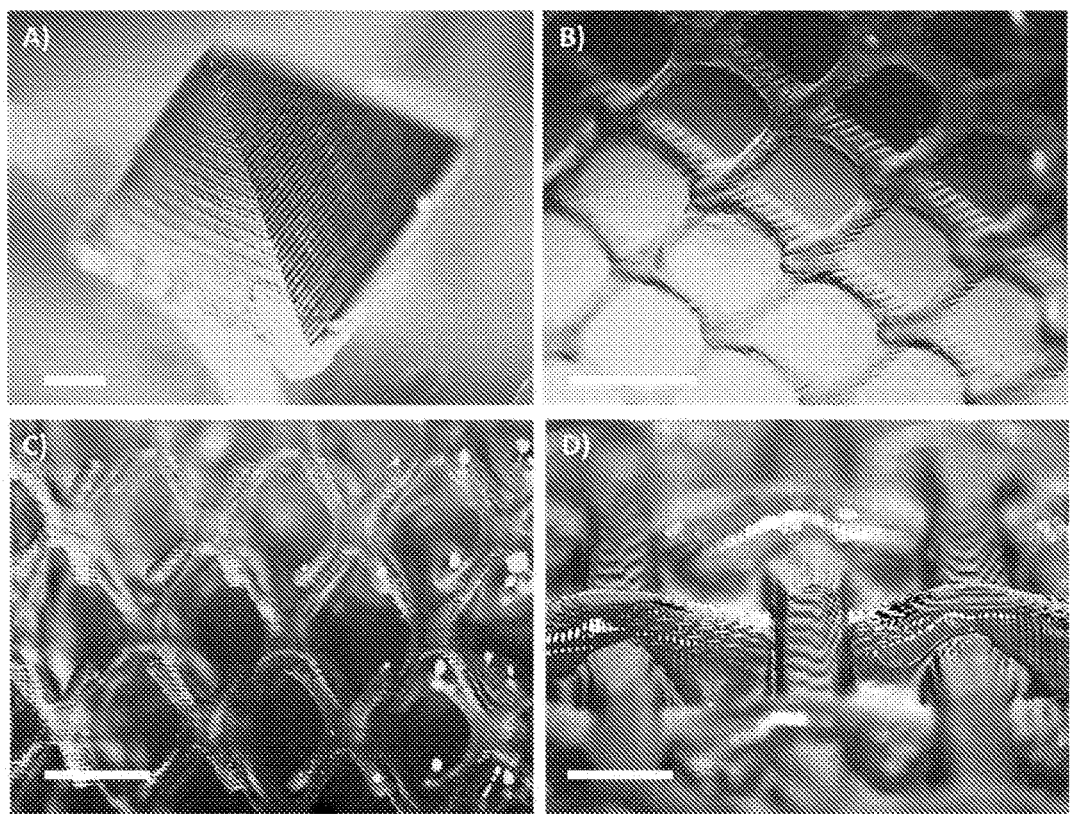
FIG. 14 shows different complex porous PVA-MA hydrogel structures fabricated using light projection stereolithography (Scale bar=500 μm).
Figure 15:
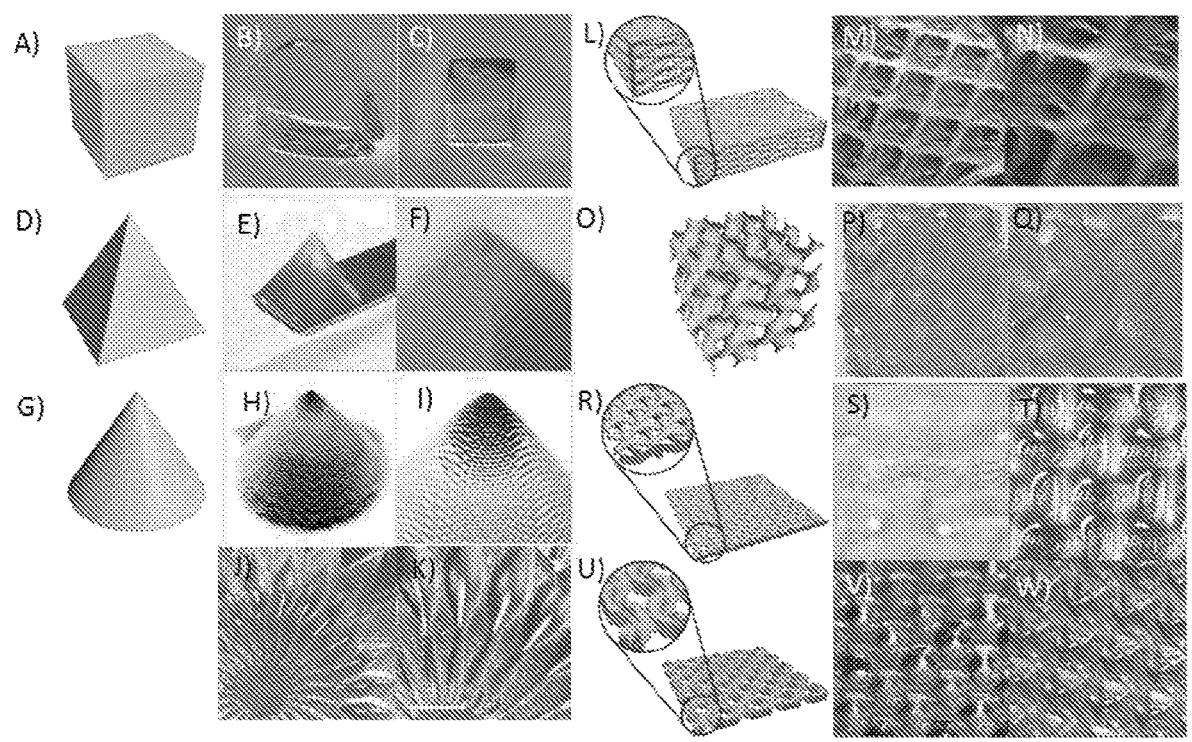
FIG. 15 shows hydrogel constructs bioprinted using DLP: cube (A-C), pyramid (D-F), cone (G-I), flower (J-K), porous lattice (L-N), porous gyroid (O-Q), woven mat (R-T) and chain mail (U-W).

The visible light+Ru/SPS system can also be combined with bio-resins to fabricate complex hydrogel constructs using light projection stereolithography or similar 3D printing or lithography technologies using visible light or lasers for curing or polymerization of bio-resins with or without cell encapsulation. FIG. 11 shows that porous and layered PVA-MA hydrogel constructs can be printed using a conventional stereolithography machine. Complex designs such as porous gyroid structures can also be fabricated where the end product is identical to the designed construct (FIG. 12). Another major advantage of using stereolithography is the high resolution as demonstrated in FIGS. 13-15 where woven mat structures with detailed topology architecture can be engineered.

PVA-MA is a cytocompatible, water soluble macromer with no batch to batch variability, where the resulting hydrogel offers tailorable physico-mechanical properties. FIG. 15A shows an attempt to print a simple cube design from a "bio-resin" of 10 wt % PVA-MA and 0.2/2 mM Ru/SPS by exposing each layer to 10 seconds of 1 mW/cm$^2$ light (irradiation dosage of 10 mJ/cm$^2$), using a step size of 50 μm. It was observed that hydrogel constructs can be successfully fabricated from this resin composition using a commercially available digital light processing (DLP) apparatus (FIG. 15B). The ability to form hydrogels from the low irradiation dosage tested also highlighted the high reactivity of Ru/SPS photo-initiators compared to other photo-initiating systems such as I2959. A small concentration of dye/photo-absorber (e.g. 1 wt % of Ponceau Red 4R) was added as a third component to the "bio-resin", which successfully minimised light scattering and resulted in constructs of dimensions as designed (FIG. 15C).

Solid hydrogel constructs with pyramid shapes (FIGS. 15D-15F) and cone shapes (FIGS. 15G-15I) were also successfully printed using this resin composition, where voxels/step sizes of 50 μm were clearly visible. Flower-like structures (FIGS. 15J and 15K) demonstrated the possibility to fabricate hydrogels with channels ranging from 50 μm to 500 μm in one print. Porous constructs were also fabricated such as the lattice structure shown in FIG. 15L printed with self-supporting and interconnecting pores. In this structure the generated strut diameter was 100 μm and the distance between struts was 500 μm (FIGS. 15M and 15N). The resolution of DLP was further highlighted when complex designs were biofabricated such as the gyroid (FIG. 15O) featuring highly curved surfaces of pore size (500 μm) and high porosity (FIGS. 15P and 15Q). The observed porosity and interconnected networks are essential for nutrient diffusion as well as integration and formation of new tissue when developing cell-laden hydrogel constructs. Moreover, sophisticated designs that cannot be obtained through any other additive manufacturing technique can also be printed using this DLP technique. Examples include the woven mat (FIGS. 15R-15T) and ring mail (FIGS. 15U-15W) which consist of intricately intertwined struts. Especially in the woven mat structures (FIG. 15S), steps of 30 μm were visible in the z-direction on the struts, corresponding to the height of each printed layer, and further outlining the high resolution that can be achieved using DLP. This observation indicates the possibility of using the developed "bio-resin" and DLP to design hydrogel constructs with highly defined surface topologies.

Figure 16:
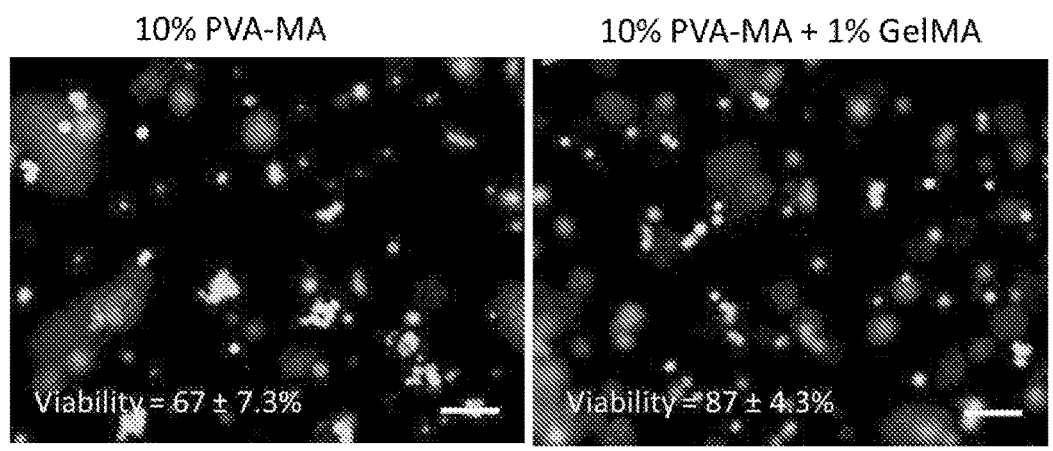
FIG. 16 shows PVA-MA or PVA-MA+Gel-MA cell-laden hydrogel constructs printed using light projection stereolithography (Scale bar=100 μm).

It was also shown that cell-laden constructs can be made using this approach, where the plain PVA-MA bio-resin yielded cell viability of ~87%. PVA-MA is a synthetic polymer and lacks the biological recognition sites for cellular signalling and function. Thus, Gel-MA, which is known to support cell adhesion, growth and proliferation, was co-polymerised with PVA-MA to impart bio-functionality to the resultant biosynthetic hydrogels. Cell viability was shown to be further improved (Example 17) where incorporation of 1 wt % Gel-MA into the PVA-MA bio-resin successfully enhanced cell viability to ~92% (FIG. 16).

Sol-gel analysis was conducted to evaluate the physico-mechanical properties of both PVA-MA and PVA-MA/Gel-MA hydrogel discs printed using DLP. It was found that there are no significant differences in terms of sol fraction (~25%), mass swelling ratio (q ~9), mesh size (~260 Å) and crosslinking density (~1.3 mol/L) between the samples with or without Gel-MA. Moreover, the PVA-MA/Gel-MA hydrogels were evaluated to have a compressive modulus of 63.2±9 kPa, which is significantly higher than pure PVA-MA gels (45.9±6 kPa, $p<0.001$).

Figure 17:
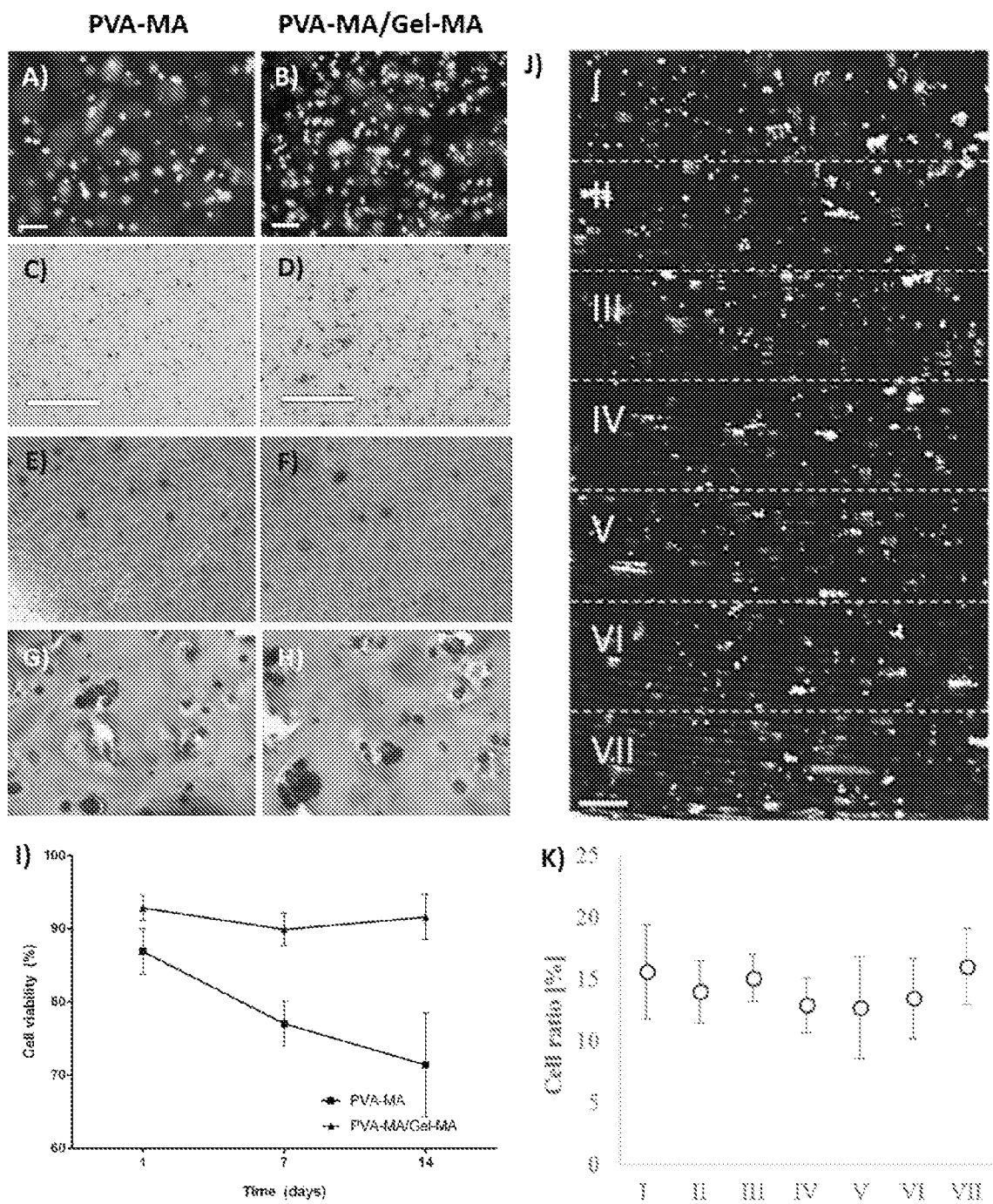
FIG. 17 shows cell encapsulation in printed hydrogel constructs. Live dead images of printed MSCs cultured in osteogenic differentiation media after 14 days: PVA-MA (A), PVA-MA/Gel-MA (B). Alkaline phosphatase staining (red) of MSCs encapsulated in PVA-MA (C) and PVA-MA/Gel-MA (D) after 7 days. Alizarin red staining (red) of MSCs encapsulated in PVA-MA (E) and PVA-MA/Gel-MA (F) after 7 days. Alcian blue staining (blue) of CPCs encapsulated in PVA-MA (G) and PVA-MA/Gel-MA (H) after 21 days of culture in chondrogenic differentiation media. Cell distribution in a printed large construct, showing homogeneous cell encapsulation and no sedimentation despite of the long printing time (cube 50×50×50 mm, printing time=1.5 h): Cross-section image of construct, showing the whole height of the cube (J). Cells were fixed, and stained with ethidium homodimer and the section was divided into 7 different zones (7.1 mm height each); Percentage of cells present in each zone, relative to the total cell amount in the whole cross-section (K). Scale bar is 200 um.

Cell encapsulation studies were carried out where bone marrow derived mesenchymal stromal cells (MSCs) were incorporated into the bio-resin and cell-laden hydrogel constructs printed. It was observed that the bio-resin formulation with or without Gel-MA was not cytotoxic to the MSCs, where viabilities of the cells encapsulated in the constructs were greater than 85% 1 day post printing (FIGS. 17A and 17B). However, it was found that the presence of Gel-MA was crucial to support the long term survival of the encapsulated cells. The viability of MSCs was shown to decrease from 87±3% (1 day) to 71±7% (14 days) in pure PVA-MA gels whereas the viability of cells encapsulated within PVA-MA/Gel-MA samples remained at 92±3% after 14 days in culture. Nevertheless, both samples were able to support osteogenic differentiation of the encapsulated MSCs as reflected in positive staining of alkaline phosphatase (FIGS. 17C and 17D) and alizarin red (FIGS. 17E and 17F), after 7 and 21 days of culture in osteogenic differentiation media, respectively.

To test the potential of the bio-resin for other tissue engineering applications, equine chondroprogenitor cells (CPCs) were also encapsulated into these gels using DLP and further cultured in chondrogenic media. CPCs were able to produce extracellular matrix within the hydrogels as indicated by the positive staining of sulfated glycosaminoglycan after 21 days in culture. These results highlighted the potential of using the developed bio-resin for fabrication of cell-laden hydrogel constructs for both bone and cartilage engineering. Furthermore, the distribution of cells within the printed hydrogel construct was examined. The cells were found to be homogenously distributed throughout the printed hydrogel constructs. FIG. 17J shows the cross-section of a 50 mm thick hydrogel construct where the percentage of cells present in each zone (I—VII) from top to bottom remained constant.

The applicant has shown that a bio-resin consisting of PVA-MA, Gel-MA and Ru/SPS is compatible with the DLP technology for the fabrication of constructs with higher resolution than existing 3D printing technologies. The hydrogels were also able to support long term survival of cells, as well as promote cell differentiation. This new bio-resin system, can allow for the fabrication of complex geometries with relatively soft hydrogels, which are otherwise not obtainable with other technologies. This method has potential implications also in the generation of novel and advanced material platforms for regenerative medicine, in vitro tissue and disease models, organ-on-a-chip devices and microfluidics.

Figure 18:
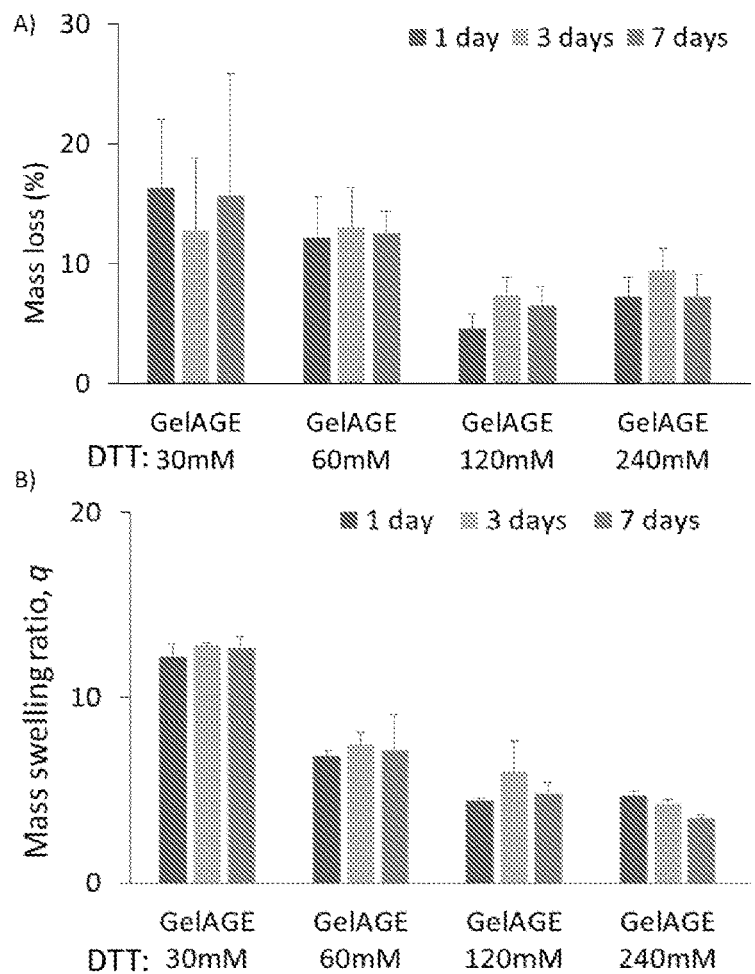
FIG. 18 shows mass loss and swelling of 20 wt % Gel-AGE gels using various DTT concentrations.

Allylated gelatin (Gel-AGE) hydrogels were investigated as an alternative to Gel-MA hydrogels. Gel-AGE gels can be prepared using the visible light+Ru/SPS system, employing a linear thiolated molecule, dithiotreitol (DTT) as the cross-linker. The physico-chemical properties of the resultant hydrogels can be tailored according to the concentration of DTT added. The gels have <20% mass loss indicating good crosslinking efficiency (FIG. 18A). Increasing the DTT concentration resulted in a reduction in mass loss indicating that a higher concentration of crosslinker leads to a higher crosslinking density, hence better crosslinking efficiency. The mass swelling ratio values also reflect the same phenomena, where increased DTT concentration resulted in lower swelling (FIG. 18B). At higher DTT concentration, the crosslinking density is also higher, forming a tighter network, therefore restricting the amount of water imbibed in the hydrogel. These results show the tailorability of the Gel-AGE platform, where the physico-chemical properties of the gels can be tuned to match the desired tissue of interest by varying the crosslinker concentration. There were also changes in the mass loss and swelling values from 1 day to 7 days.

Figure 19:
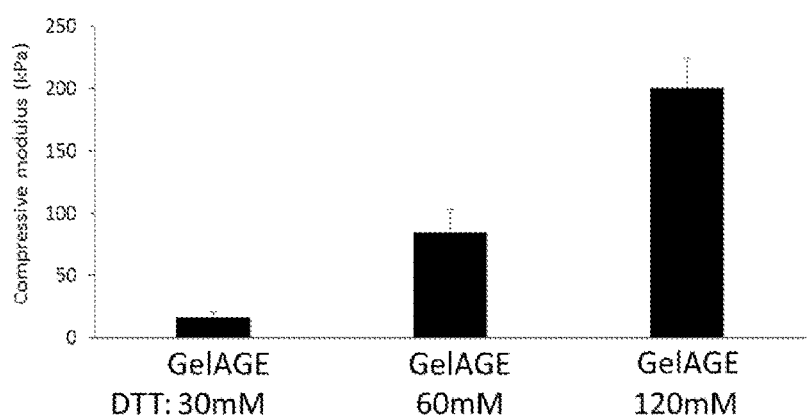
FIG. 19 shows compressive modulus of 20 wt % Gel-AGE gels crosslinked using 1/10 Ru/SPS (mM/mM) and 3 minutes of 30 mW/cm$^2$ visible light.

By changing the concentration of DTT, the resultant hydrogels also have different mechanical properties. FIG. 19 shows that the compressive modulus of Gel-AGE gels increases with increasing DTT concentration. This result is in accordance with results obtained from the mass loss and swelling study, where higher DTT concentration yielded gels or lower sol fraction and higher mass swelling ratio, which indicates formation of a higher crosslinked network. This high crosslinking density accounts for the high compressive modulus observed.

Figure 20:
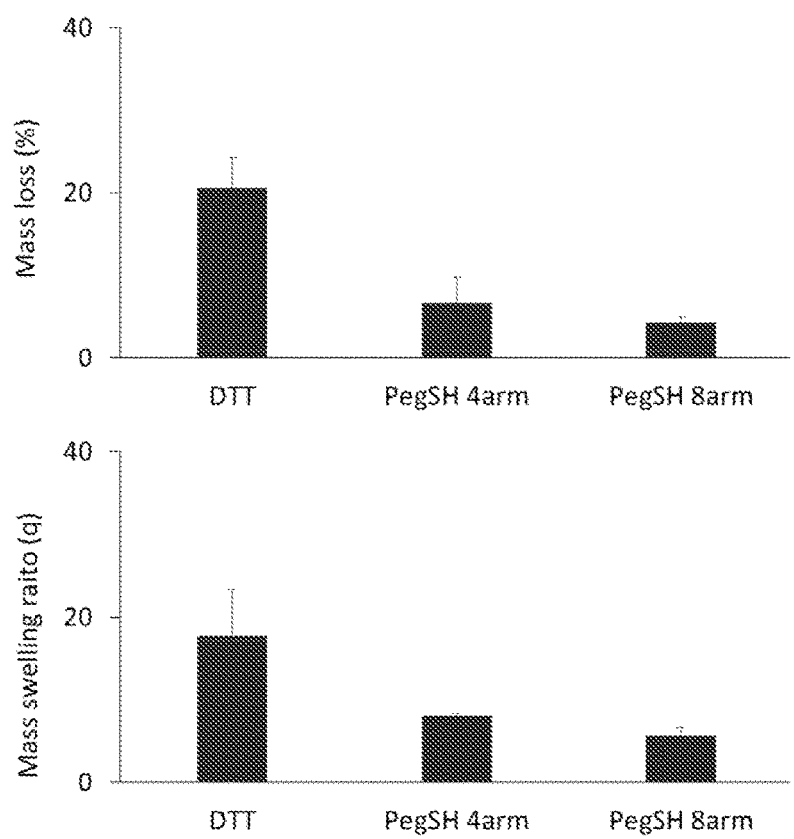
FIG. 20 shows mass loss and swelling ratio of 20 wt % Gel-AGE gels crosslinked using DTT, PEGSH-4arm or PEGSH-8arm. Final concentration of thiols is kept at 30 mM. Photoinitiator concentration used is 1/10 Ru/SPS (mM/mM) and 3 minutes of 30 mW/cm$^2$ of visible light.

The physico-mechanical properties of the Gel-AGE gels can also be tailored depending on the chemical structure of the thiolated molecules (FIG. 20). The effects of using three different thiolated molecules (DTT, PEGSH-4arm and PEGSH-8arm) on the mass loss and swelling properties of the Gel-AGE gels were compared. As expected, the gels formed by a linear thiolated molecule (DTT, MW=154.23 Da) have a higher sol fraction and mass swelling ratio compared to the thiolated PEGs (both 4arm and 8arm with MW of 10 kDa). Employing larger thiolated molecules increases the accessibility of the AGE groups grafted onto the gelatin, allowing easier step-growth polymerization between the AGE and thiol groups.

Figure 21:
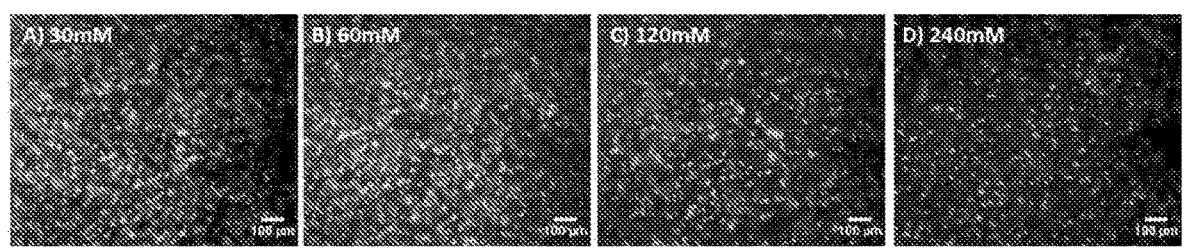
FIG. 21 shows live/dead images of HAC encapsulated in Gel-AGE hydrogels after 7 days in culture using various concentrations of DTT: A) 30 mM; B) 60 mM; C) 120 mM; D) 240 mM. Scale bar=100 μm.
Figure 22:
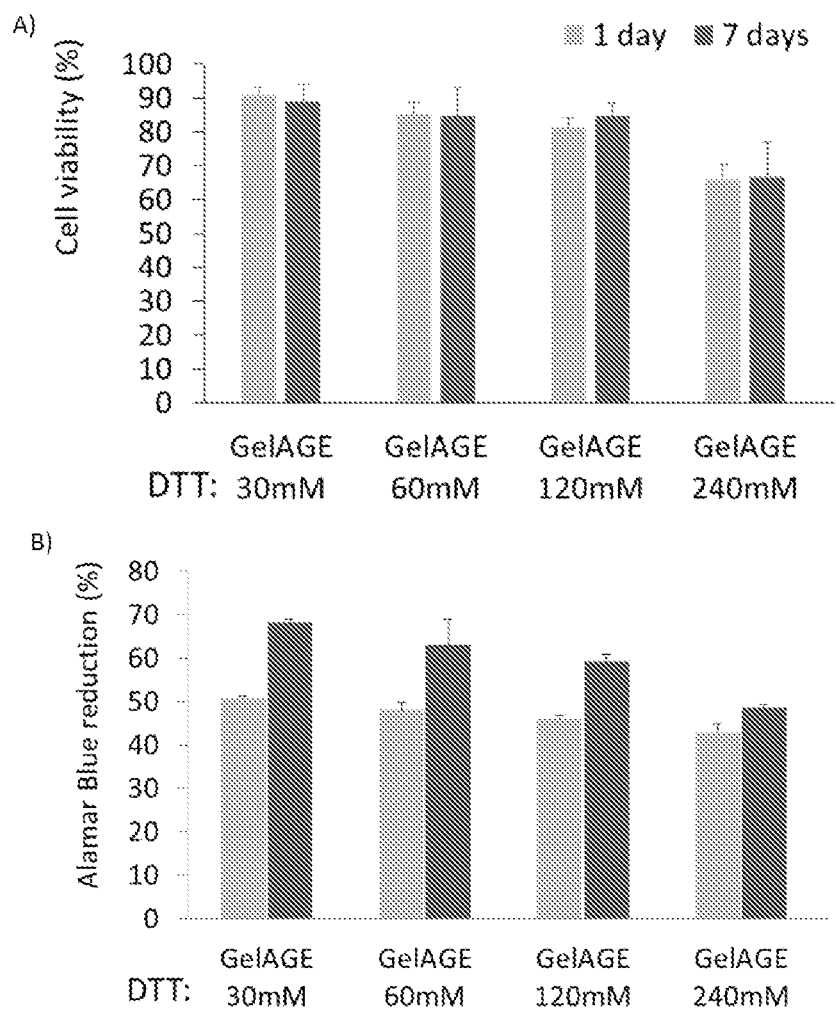
FIG. 22 shows A) cell viability and B) metabolic activity of HAC encapsulated in Gel-AGE hydrogels using various concentrations of DTT.

HAC were encapsulated into Gel-AGE hydrogels and evaluated for both viability as well as metabolic activity. Live/dead images showed that viability of HAC was high in all samples after 7 days in culture (FIG. 21). Increasing DTT concentration resulted in a decrease in viability (FIG. 22). This result was not unexpected as DTT is known to be a potent reductant, and able to reduce the cell membrane lipid bilayer causing cell death. Total metabolic activity of cells was shown to increase from 1d to 7d of culture, indicating that cells were able to proliferate in the Gel-AGE gels (FIG. 21B). Once again, increasing DTT concentration led to a decrease in metabolic activity, which is in agreement with the cell viability studies. By correlating the cell encapsulation studies to the mass loss and swelling studies, it was found that 120 mM of DTT is the optimum for fabricating gels and for lowest mass loss while still retaining maximum cell viability.

Figure 23:
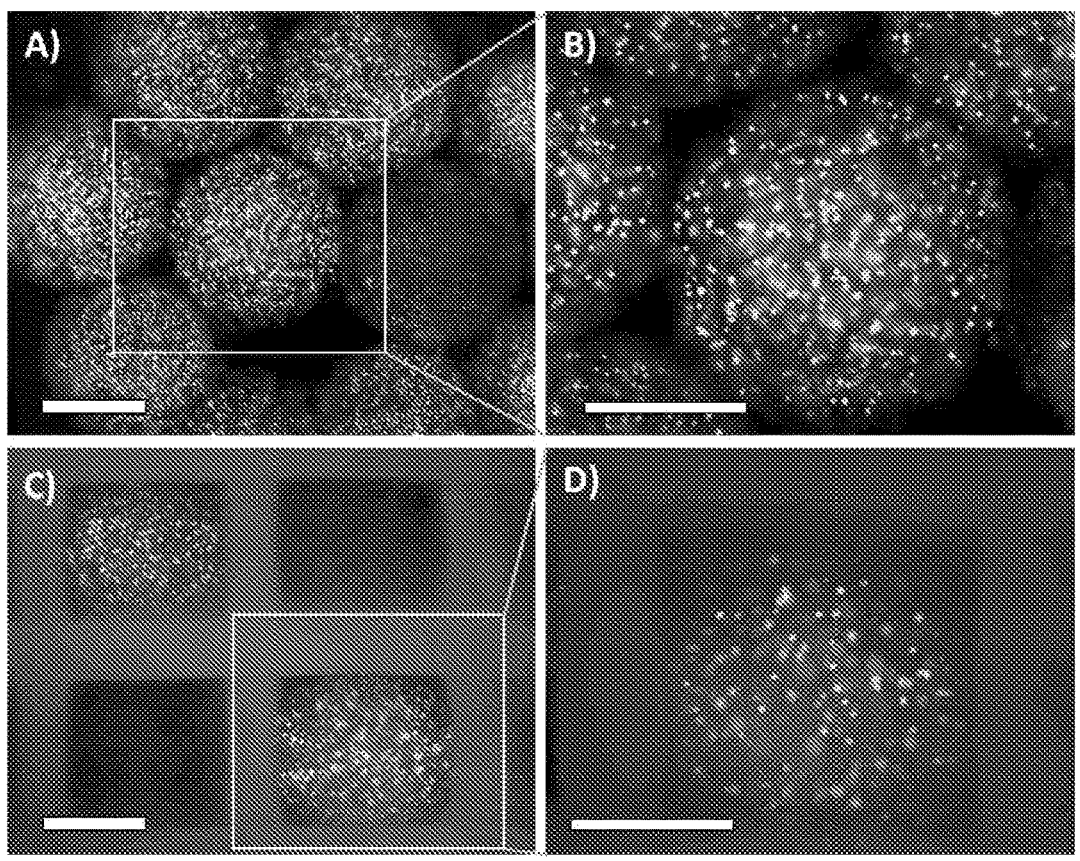
FIG. 23 shows Gel-MA cell-laden hydrogel beads fabricated using a micro-fluidic approach.

A micro-fluidic approach may also be employed to fabricate hydrogel beads or a continuous hydrogel fibre using the visible light+Ru/SPS system. Cells may also be encapsulated in the hydrogel beads or fibres and contain single or multiple cell types (i.e. co-culture). Example 23 shows that human breast adenocarcinoma cells (MDA-MB-231) can be successfully encapsulated into Gel-MA hydrogel beads and show high viability (FIG. 23). It will be appreciated by those skilled in the field that other types of cells, such as chondrocytes and mesenchymal stem cells, or co-cultures of cells, may also be encapsulated in hydrogel beads in a similar manner. These beads or fibres can also be assembled into other 3D printed constructs to form macro-tissues for 3D cancer drug screening or for tissue engineering applications. It is anticipated that micro-fluidic approaches may be used to fabricate single or multi-layered hydrogel beads encapsulated with cells as well as therapeutic agents, such as proteins, growth factors or drugs, for controlling the release rate of a therapeutic agent in tissue engineering applications.

Other biological molecules can also be incorporated into Gel-MA hydrogels as a measure to direct specific cellular signaling for certain applications. As an analogue of heparin sulfate which occurs naturally in the native cartilage extracellular matrix, heparin has been incorporated to further enhance the chondrogenic capacity of Gel-MA hydrogels. Example 29 shows the covalent incorporation of Hep-MA into Gel-MA hydrogels fabricated as casted discs or beads (using the micro-fluidics). The retention of Hep-MA is high in Gel-MA/Hep-MA gels fabricated using both techniques.

Figure 27:
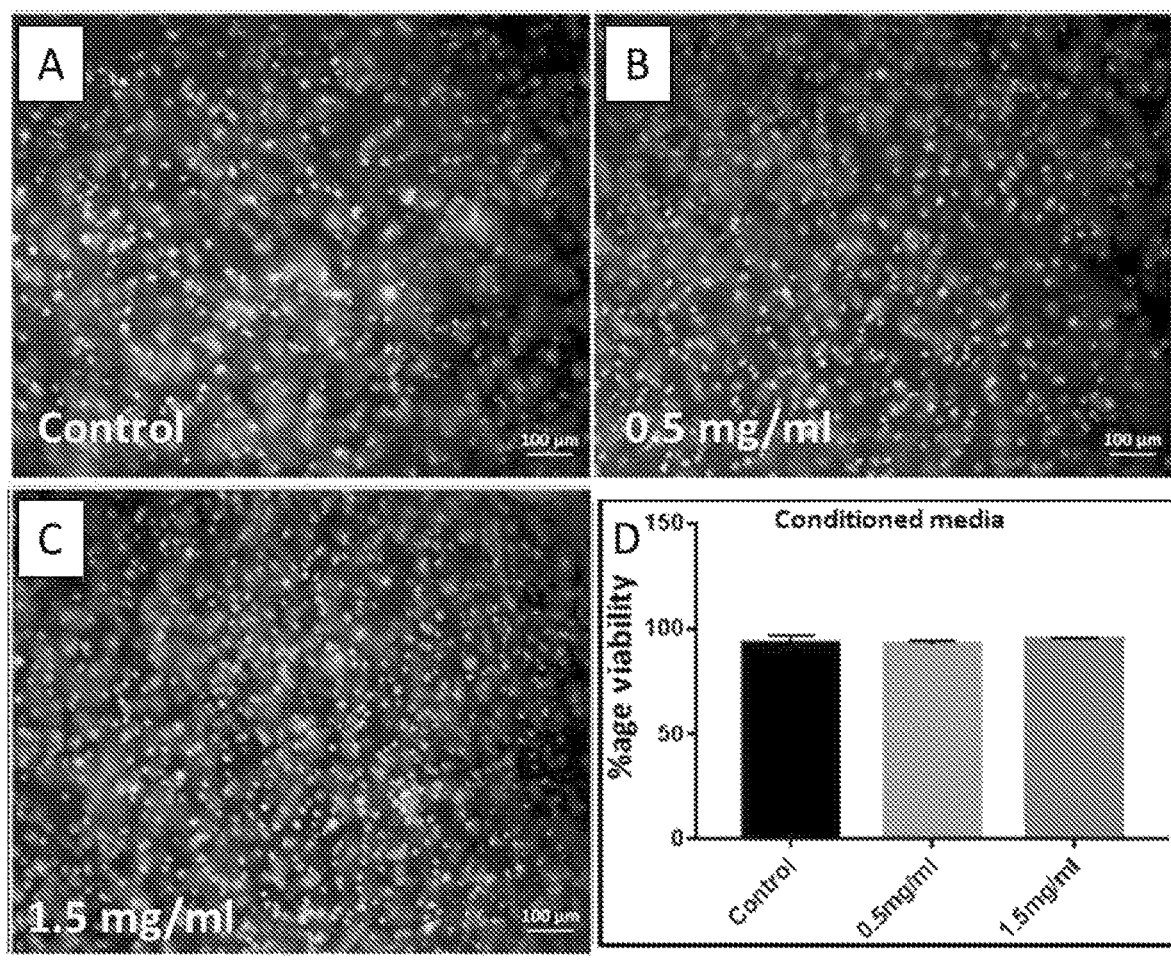
FIG. 27 shows live/dead images of MSCs encapsulated in pure 5 wt % Gel-MA hydrogels (A) or 5 wt % Gel-MA hydrogels incorporated with 0.5 mg/ml MgCO$_3$ (B) or 1.5 mg/ml MgCO$_3$ (C). Cell viability of MSCs encapsulated in Gel-MA hydrogels with and without MgCO$_3$ nanoparticles (D).
Figure 28:
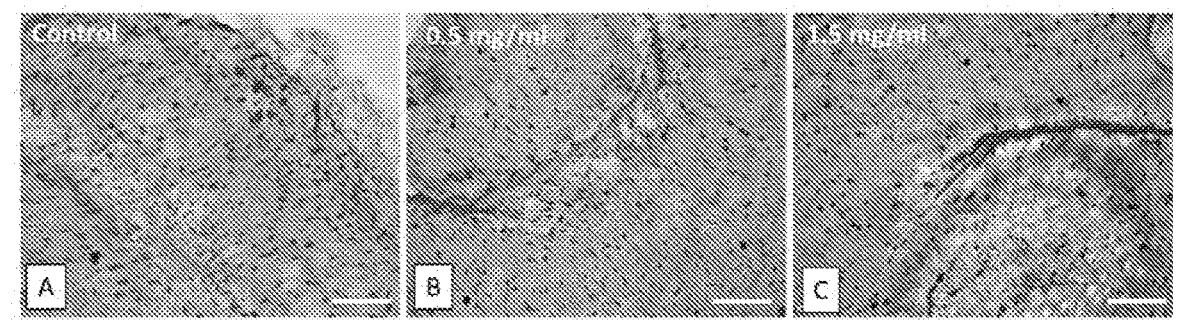
FIG. 28 shows histology sections of MSCs encapsulated in Gel-MA hydrogels with or without MgCO$_3$ nanoparticles, stained with Alizarin red: A) Control—no nanoparticles; B) 0.5 mg/ml $MgCO_3$; C) 1.5 mg/ml $MgCO_3$. Red indicates mineralisation as a measure of bone formation.

Nanoparticles can also be incorporated into Gel-MA hydrogels either for mechanical reinforcement or for added biofunctionality. For example, magnesium ions have been known to stimulate bone growth. Hence, magnesium based nanoparticles—magnesium carbonate ($MgCO_3$)—were incorporated into Gel-MA hydrogels, and the capability of these hybrid gels in stimulating osteogenic differentiation of human MSCs was investigated. It was shown that the addition of $MgCO_3$ nanoparticles did not pose any detrimental effect on the cells (FIG. 27 live/dead—high viability), where encapsulated MSCs were able to mineralise within the hydrogel matrix (FIG. 28 Alizarin red staining).

The inventors tested a further type of unsaturated ester group (norbornene-bicyclo[2.2.1]hept-2-ene) using the visible light system, and showed that the gels formed again have tailorable physico-chemical properties with a high potential for use in 3D bioprinting and tissue engineering applications, in particular bone prevascularisation applications. The outcome of Example 32 is that visible light initiators are compatible with the thiol-norbornene step-growth polymerisation. It was also observed that the mass swelling ratio decreases in conjunction with the decrease in sol fraction values. Example 33 shows that gelatin-norbornenyl hydrogels can be used for soft tissue engineering, such as prevascularisation of bone scaffolds.

Any reference to prior art documents in this specification is not to be considered an admission that such prior art is widely known or forms part of the common general knowledge in the field.

As used in this specification, the words "comprises", "comprising", and similar words, are not to be interpreted in an exclusive or exhaustive sense. In other words, they are intended to mean "including, but not limited to.

The invention is further described with reference to the following examples. It will be appreciated that the invention as claimed is not intended to be limited in any way by these examples.

EXAMPLES

Materials and Methods

Gelatin (porcine skin, type A, 300 g bloom strength), poly(vinyl alcohol) (13-23 kDa, 98% hydrolysed), phosphate buffered saline (PBS), methacrylic anhydride, cellulose dialysis membrane (10 kDa molecular weight cut-off), collagenase type II, L-ascorbic acid-2-phosphate, tris(2,2-bipyridyl)dichlororuthenium(II) hexahydrate (Ru), sodium persulfate (SPS), calcein-AM, Propidium Iodide (PI), proteinase K, dimethyl-methylene blue (DMMB), safranin-O, chondroitin sulphate A (CS-A) and L-proline were purchased from Sigma-Aldrich. Dulbecco's Modified Eagle's Medium (DMEM) high glucose, 4-(2-hydroxyethyl)-1-piperazine-ethanesulfonic acid (HEPES), foetal calf serum (FCS), 0.25% trypsin/EDTA, and penicillin-streptomycin (PS), were purchased from Invitrogen. Medical grade silicone sheets were obtained from BioPlexus. Cell strainers (100 μm) were bought from BD Biosciences. AlamarBlue® reagent was obtained from LifeTechnologies. CyQUANT® cell proliferation assay kit was purchased from ThermoScientific. Gill's hematoxylin solution was obtained from Merck Millipore. Optimal cutting temperature compound (OCT) was obtained from VWR International.

Example 1: Synthesis of Gelatin-Methacryloyl (Gel-MA) Hydrogel

Gelatin was dissolved in PBS at a 10 wt % concentration. 0.6 g of methacrylic anhydride per gram of gelatin was added to the gelatin solution, and left to react for 1 h at 50° C. under constant stirring, followed by dialysis against deionised water to remove unreacted methacrylic anhydride. The purified gelatin-methacryloyl solution was filtered through a 0.22 μm sterile filter then lyophilised under sterile conditions. The degree of methacrylation was quantified to be 60% using $^1$H-proton nuclear magnetic resonance (Bruker Avance 400 MHz).

Dried sterile Gel-MA was dissolved in PBS at 37° C. and left to cool overnight at RT. Prior to crosslinking, Ru and SPS were added to the Gel-MA solution, scooped into the silicon moulds (5 mm diameter×1 mm thickness) on a glass slide and sandwiched with a cover slip. The samples were then irradiated under visible light (OmniCure® S1500, Excelitas Technologies). The light was irradiated through a light filter (Rosco IR/UV filter) where only light of the wavelength 400-450 nm was allowed to pass through. A variety of initiator concentrations (0.1/1, 0.2/2 and 0.3/3 of Ru/SPS (mM)), light intensities (10, 20 and 30 mW/cm$^2$), and exposure time (0.5, 1, 3, 5, 10 and 15 minutes) were studied to optimise the irradiation conditions. The optimal conditions were found to be: visible light intensity of 30 mW/cm$^2$, initiator concentration of 0.2/2 Ru/SPS (mM), and at least 3 minutes of exposure time.

Example 2: Cartilage Excision, Chondrocyte Isolation and Expansion

Articular cartilage biopsies were harvested with ethics approval from a consenting 28 year old female patient. The cartilage was diced into 1 to 2 mm cubes and digested overnight at 37° C. with 0.15% w/v collagenase type II in basic chondrocyte media (DMEM high glucose media supplemented with 10% FCS, 10 mM HEPES, 0.2 mM L-ascorbic acid-2-phosphate, 0.4 mM L-proline and 1% PS). The resulting suspension was filtered through a 100-μm cell strainer (BD Biosciences) to exclude the undigested tissue and centrifuged at 700-g for 4 min. The isolated chondrocytes (HAC) were cultured in basic chondrocyte media and expanded at 37° C. in a humidified 5% CO2/95% air incubator.

Example 3: Photo-Toxicity and Radical Toxicity Evaluation

The toxicity of the visible light initiated radical polymerisation system of Example 1 was evaluated using the expanded HAC from Example 2. HAC in culture flasks were trypsinised, suspended in basic chondrocyte media, and seeded in 48 well plates at a concentration of 50 HACs/mm$^2$. The cells were firstly allowed to attach to the surface for 4 hours, then exposed to either 30 mW/cm$^2$ of UV or visible light (15 minutes), with or without 0.05 wt % of 12959 or 0.2/2 Ru/SPS (mM) respectively. The samples were then incubated in a humidified 5% CO2/95% air incubator at 37° C. and replenished with fresh media after 3 days. After 1 and 7 days, the cells were visualised and quantified using the live/dead assay. ImageJ (version 1.46, National Institutes of Health) was used to count the cells. The results are shown in FIG. 1.

Example 4: HAC Encapsulation in Gel-MA Hydrogels

Expanded HACs from Example 2 were trypsinised and suspended in basis chondrocyte media. The cell suspension was added to the macromer solution containing initiators to give a final concentration of 2.5×10$^6$ HACs/ml. The cell-laden gels were then fabricated according to Example 1. The irradiation conditions were 15 minutes of light (30 mW/cm$^2$ for both UV and visible light), where initiator concentrations were kept at 0.05 wt % 12959 or 0.2/2 Ru/SPS (mM) respective to the light source. Live/dead, alamarBlue, glycosaminoglycan (GAG) and DNA assays were performed on the samples at after 1, 7, 14 and 21 days in culture. The results are shown in FIG. 2.

Example 5: Live/Dead Assay

Samples of the Gel-MA hydrogel from Example 4 were firstly washed with PBS then stained with 1 ug/ml of Calcein-AM and PI for 10 minutes. The cells will stain green if alive and red if dead. After staining, the gels were washed with PBS for three times before imaging them using a fluorescence microscope (Zeiss axioimager Z1). The cells were quantified using the ImageJ software and the cell viability was calculated using the equation below:

$$\text{Viability (\%)} = \frac{\text{number of live cells}}{\text{number of live cells} + \text{dead cells}} \times 100$$

The results of the live/dead assay are shown in FIG. 2.

Example 6: AlamarBlue Assay

AlamarBlue assay was performed according to the manufacturer's protocol. Samples of the Gel-MA hydrogel from Example 4 were incubated in basic chondrocyte media containing 10% (v/v) alamarBlue® reagent for 24 hours. The alamarBlue reagent is reduced from blue to red/pink colour for cells that remain metabolically active. The reduction in alamarBlue reagent was calculated using the equations provided by the manufacturer after measuring the absorbance at 570 nm, using 600 nm as a reference wavelength (Fluostar Galaxy BMG Labtechnology). The results are shown in FIG. 3.

Example 7: Glycosaminoglycan (GAG) and DNA Assay

Cell-laden Gel-MA samples were digested overnight in 200 μL of 1 mg/ml proteinase-K solution at 56° C. In order to quantify the amount of GAG retained in the gel, the digested samples were reacted with DMMB. The absorbance of the samples was then measured at 492 nm (Fluostar Galaxy BMG Labtechnology). The GAG concentrations were calculated from a standard curve constructed using known concentrations of CS-A. The amount of DNA in the gels was measured using the CyQUANT kit. The cells in the digested samples were firstly lysed and RNA degraded using the provided lysis buffer with RNase A (1.35 KU/ml) added for 1 hour at RT. GR-dye solution was then added to the samples, incubated at RT for 15 minutes then the fluorescence was measured (Fluostar Galaxy BMG Labtechnology). A standard curve was constructed using the DNA provided in the kit. The results are shown in FIGS. 4A, 4B and 4C.

Example 8: Histological Examination

The cell-laden constructs were fixed in 10% formalin for 1 hour and then embedded in OCT. The samples were cryo-sectioned (10 um per slice) and then stained with haemotoxylin for cells and safranin-O for glycosaminoglycans. The results are shown in FIG. 4D.

Example 9: Preparation of Gel-MA/Collagen Hydrogel

Dried sterile Gel-MA was dissolved in sterile PBS at a concentration of 20 wt %. Collagen solution (1.7 wt %) was added to the Gel-MA solution at a 1:1 ratio. The final concentration of macromer solution was 10 wt % Gel-MA and 0.85 wt % collagen. The hydrogel was prepared from this solution as outlined in Example 1.

Example 10: Shear Stress of Gel-MA/Collagen Macromer Solution

Figure 5:
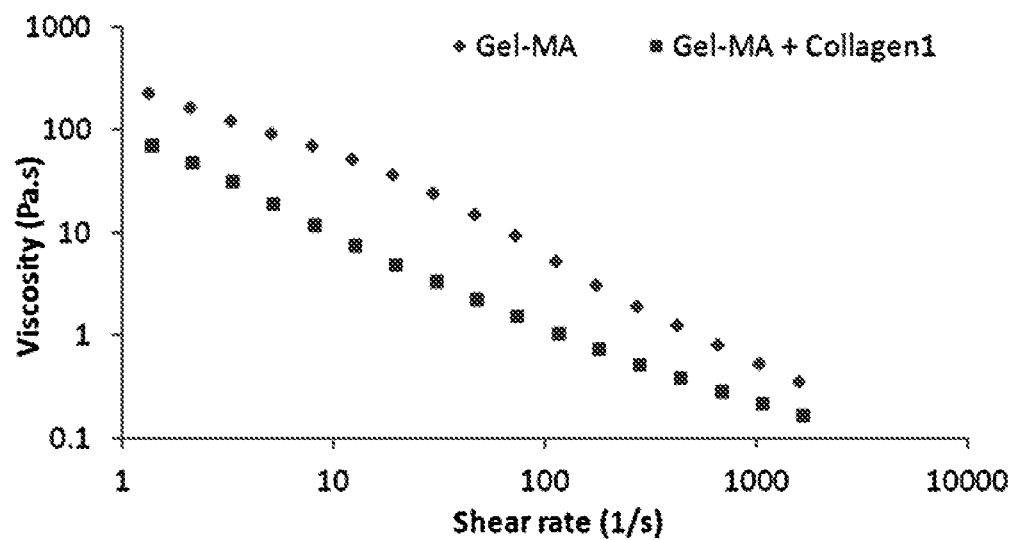
FIG. 5 shows viscosity vs shear rate of Gel-MA and Gel-MA+Collagen 1 macromer solutions, temperature was kept constant at 20° C.

Rheological properties of bio-ink (10 wt % Gel-MA+0.85 wt % collagen) were measured using a 40 mm parallel plate setup (TA instruments). Measurements were conducted at 20° C. with increasing shear rate from 1/s to 1200/s. The results are shown in FIG. 5.

Example 11: Deformation of Thickness of Gel-MA/Collagen Hydrogel

Hydrogel discs were prepared by casting 10 wt % Gel-MA+0.85 wt % Collagen 1 macromer solution into disc moulds. The constructs were then irradiated for 15 minutes in the presences of a photo-initiator and a light source, where the surfaces of the constructs were exposed to oxygen. In a first experiment, the light intensity was kept at 3 mW/cm$^2$ whereas the photo-initiator concentrations were varied from 0.05 to 0.5 wt % and 0.2/2 mM to 2/20 mM for 12959 and Ru/SPS respectively. In a second experiment the light intensity was varied from 3 to 100 mW/cm$^2$ while keeping the photo-initiator concentrations constant at 0.05 wt % and 0.2/2 mM for 12959 and Ru/SPS respectively. The level of oxygen inhibition was characterised as the deformation of thickness before ($t_0$) and after equilibrium swelling ($t_s$). The deformation of thickness is given by the equation: Deformation of thickness=$[(t_0-t_s)/t_0] \times 100$. The results are shown in FIGS. 6 and 7.

Example 12: Cell Viability of MCF-7 in Gel-MA/Collagen Hydrogel

Breast adenocarcinoma cells (MCF-7) were mixed into 10 wt % Gel-MA+0.85 wt % Collagen 1 macromer solution at a concentration of 2.5 million cells/ml then photo-encapsulated at a various photo-initiator concentrations and light intensities. A live/dead assay was performed after 1 day to evaluate the viability of encapsulated MCF-7 cells. The results are shown in FIG. 8.

Example 13: Oxygen Inhibition in 3D Biofabricated Constructs

Figure 10:
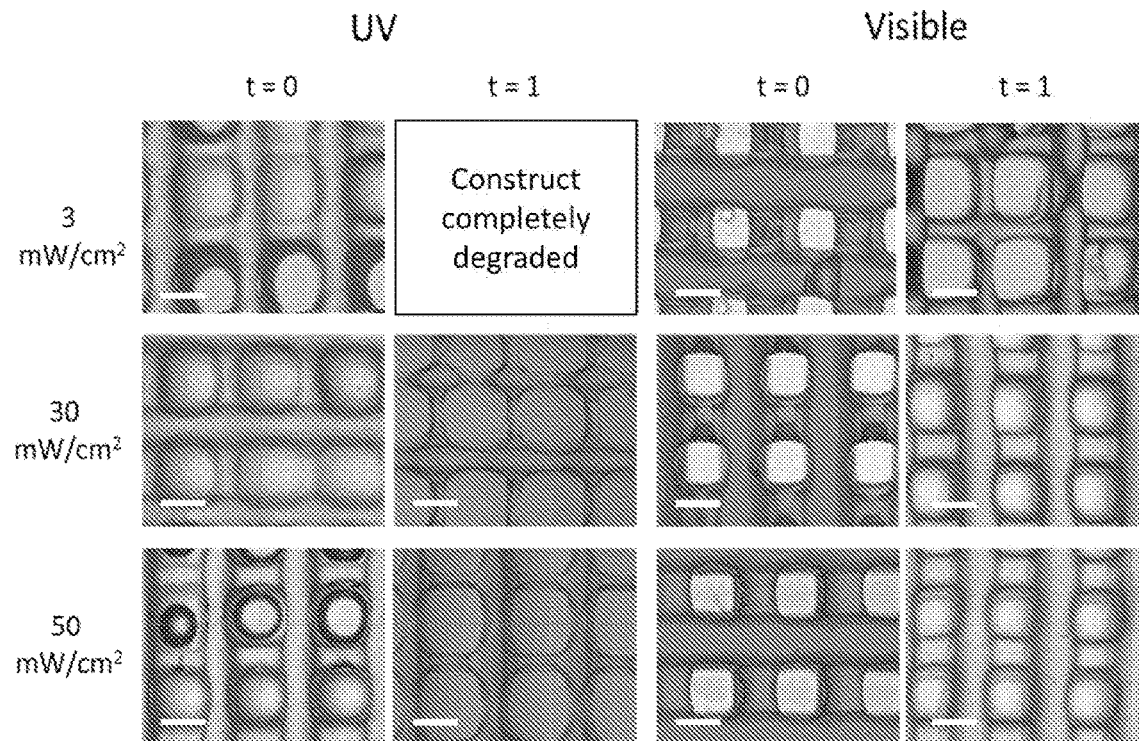
FIG. 10 shows 3D printed Gel-MA+Collagen 1 hydrogel constructs before (t=0) and after swelling (t=1) at various light intensities (Scale bar=500 μm).

The constructs were printed using the BioScaffolder dispensing system (SYS+ENG, Salzgitter-Bad, Germany). The hydrogel dispensing heads was maintained at 20° C. The bio-ink used was 10 wt % Gel-MA+0.85 wt % Collagen 1 with either 0.05 wt % 12959 or 0.2/2 Ru/SPS (mM). Constructs were printed using a 23 G needle, an XY-plane speed of 500 mm/min and a strand distance of 1.5 mm. Printed constructs were subjected to light intensities of 3, 30 and 50 mW/cm$^2$. The photo-crosslinked constructs were then imaged using a stereo microscope and are shown in FIG. 10.

Example 14: Cell Encapsulation in 3D Biofabricated Constructs

A bio-ink comprising 10 wt % Gel-MA+0.85 wt % Collagen 1+0.2/2 Ru/SPS (mM) macromer solution was mixed with breast adenocarcinoma cells (MCF-7) at a concentration of 5 million cells/ml. The bio-ink was then 3D printed as outlined in Example 13 and subjected to 50 mW/cm$^2$ of light for 15 minutes. The construct was imaged using a stereo microscope (FIG. 11A) and the viability of the encapsulated cells was assessed using a live/dead assay (FIG. 11B).

Example 15: Synthesis of Allylated Gelatin

Allylated gelatin (Gel-AGE) was synthesized using standard protocols. Gelatin was dissolved in deionized water (10 wt %) at 65° C. and different ratios of allyl glycidyl ether (4.71-29.5 mmol) and 2 M NaOH (0.79-19.65 mmol) were added. The reactions were allowed to continue for 1-24 h at 65° C. and were then dialysed (MWCO 1 kDa) against deionized water. The products were lyophilised and stored at 4° C. until use. $^1$H-NMR (300 MHz, D$_2$O): δ=7.33-7.25 (d, arom. —CH) 6.01-5.86 (m, —O—CH$_2$—CH=CH$_2$), 5.36-5.25 (t, —O—CH$_2$—CH=CH$_2$), 4.6-0.8 (m, backbone-H) ppm.

Example 16: Gel-AGE Hydrogel Fabrication

Gel-AGE hydrogels were prepared in PBS (20 wt %) and then mixed with DTT to achieve functional group ratios of 1:1.5, 1:3, 1:6 and 1:12 (allyl:SH). After the addition of a photoinitiator (1/10 mM RU/SPS), the hydrogel precursor solutions were photo-polymerised with 30 mW/cm$^2$ of visible light (Rosco IR/UV filter equipped to OmniCure® S1500, Excelitas Technologies) for 3 min. Cylindrical constructs (h=2 mm, Ø=6 mm) were prepared using custom-built moulds. After polymerization, each hydrogel was weighed ($m_{initial,t0}$) and three samples per hydrogel composition were directly lyophilised to record their initial dry weights ($m_{dry,t0}$) and determine the actual macromer weight fraction, which is reported as the ratio of the initial dry weight to the initial weight.

$$\text{Actual macromer fraction} = \frac{m_{dry,t0}}{m_{initial,t0}}$$

To determine the initial dry weight of the remaining samples, the factor of the actual macromer fraction and individual initial weight was used.

$$m_{dry,t0} = m_{initial} \times \text{actual macromer fraction}$$

The remaining samples were allowed to swell in PBS at 37° C. for up to 1 week. Swollen hydrogel samples were collected to record wet weight ($m_{swollen}$) then lyophilised to obtain the freeze dried weight ($m_{dry}$) and define the mass loss and mass swelling ratio (q) according to the following equations:

$$\text{Solfraction} = \frac{m_{dry,t0} - m_{dry}}{m_{dry,t0}} \times 100$$

$$q = \frac{m_{swollen}}{m_{dry}}$$

The sol fraction of the hydrogels is defined as percentage of macromers not crosslinked into the hydrogel network, and determined as the mass loss after equilibrium swelling (t=Id).

Example 17: Cell Encapsulation in Gel-AGE Hydrogels

Chondrocytes were harvested from macroscopically normal regions of the articular cartilage from human patients undergoing ACL reconstruction surgery at Forte health private hospital in Christchurch, New Zealand. The tissue was digested in chondrogenic expansion media (DMEM supplemented with 10 mM HEPES, 0.1 mM NEAA, 1% (v/v) penicillin-streptomycin, 0.1 mM AsAp and 10 wt.-% FBS) with 0.15 wt.-% type II collagenase at 37° C. in a humidified air incubator (5% $CO_2$/95% air) overnight. The solution was filtered through a cell strainer and isolated chondrocytes were expanded in high-density monolayers (BD Biosciences tissue culture flasks) for three passages cultured in chondrogenic expansion media. Cells were then encapsulated in Gel-AGE hydrogels at a concentration of $15 \times 10^6$ cells/mL and cultured for 1 week in chondrogenic differentiation media (dulbecco's DMEM supplemented with 10 mM HEPES, 0.1 mM NEAA, 1×ITS+1, 1% (v/v) penicillin-streptomycin, 0.4 mM L-proline, 0.2 mM BSA, 0.2 mM AsAp, 0.1 µM dexamethasone and 10 ng/mL TGFb-1). Cell free hydrogels served as negative control group.

Example 18: Gel-AGE Hydrogel Live/Dead Viability Assay

Samples of Gel-AGE hydrogels prepared according to Example 16 were assayed according to the procedure of Example 5. The results are shown in FIG. 21.

Example 19: Gel-AGE Hydrogel AlamarBlue Metabolic Activity

Samples of Gel-AGE hydrogels prepared according to Example 16 were assessed for metabolic activity using the procedure of Example 6. The results are shown in FIG. 22.

Example 20: Synthesis of Poly(Vinyl Alcohol)-Methacryloyl (PVA-MA)

PVA-MA was prepared by reacting PVA with methacrylic anhydride in water. In a typical experiment, a 10 wt % PVA solution was prepared by heating PVA in water at 80° C. until the PVA was completely dissolved. The PVA solution was then left to cool to room temperature prior to the addition of methacrylic anhydride (0.375 ml per g of PVA) and the solution was left to react for 4 hours. The pH of the reaction solution was adjusted to 8 every hour. To stop the reaction, the solution was precipitated in acetone. The precipitated polymer was then re-dissolved in water and then further purified by dialysis against water through a 10 kDa molecular weight cut-off membrane. Lastly, the purified solution was lyophilized to obtain dried PVA-MA.

Example 21: Fabrication of Constructs Using Light Projection Stereolithography Based Approaches Constructs were fabricated using the Perfactory® 4 Standard (EnvisionTec, Gladbeck, Germany). The bio-resin used was 10 wt % PVA-MA+1 wt % photo-absorber with or without 1 wt % Gel-MA. The initiator concentration used ranged from 0.2/2 to 0.5/5 Ru/SPS (mM). Constructs were printed by exposing each layer (50 µm) to 10 mJ/cm² of light. Sol-gel analysis was conducted to evaluate the physico-mechanical properties of the printed constructs (Ø5×1 mm cylinders). For cell encapsulation studies, human mesenchymal multipotent stromal cells (hMSCs) and equine chondroprogenitor cells (CPCs) were mixed with the resin at a final density of $5 \times 10^6$ and $20 \times 10^6$ cells/ml respectively prior to light projection. The printed constructs were then imaged using a stereo microscope and are shown in FIGS. 12 to 15.

Example 22: Cell Encapsulation in Constructs Fabricated Using Light Projection Stereolithography Mouse teratocarcinoma cells (ATDC5) were mixed into the 10 wt % PVA-MA+0.5/5 Ru/SPS (mM)+1 wt % photo-absorber, with or without 1 wt % Gel-MA. Hydrogel discs (5 mm diameter×0.5 mm thickness) were printed using the same conditions outlined in Example 14. The viability of cells post printing were assessed using a live/dead assay and are shown in FIG. 16.

Example 23: Fabrication and Cell Encapsulation in Hydrogel Beads

Cell-laden Gel-MA hydrogel beads were fabricated using a microfluidic device consisted of PTFE tubing, T-junctions and a fused silica capillary. The continuous phase was sunflower oil where the dispersed phase was a 20 wt % Gel-MA bio-ink+0.2/2 Ru/SPS (mM) mixed with human breast adenocarcinoma cells (MDA-MB-231) at a concentration of 10 million cells/ml. The oil and hydrogel solution were pumped through the device at a rate of 1 ml/min and 50 µl/min respectively. The hydrogel beads were sheared off by the oil and subjected to 100 mW/cm² of visible light for crosslinking. The overall exposure time was kept to 3 minutes. The hydrogel beads were then stained for live/dead to evaluate viability of cells post encapsulation. The results are shown in FIG. 23.

Example 24: Fabrication and Cancer Cell Encapsulation Gel-MA Hydrogel Microspheres Experiments were carried out with human ovarian adenocarcinoma cell lines (SKOV3) and normal human foreskin fibroblasts (HFF). SKOV3 and HFF were cultured in media containing DMEM (high glucose, GlutaMAX Supplement, pyruvate) (GIBCO, USA) with 5% foetal bovine serum (FBS; GIBCO, New Zealand), 100 units/mL penicillin (GIBCO, USA) and 100 µg/mL streptomycin (GIBCO, USA). The cells were seeded at a density of 3,000 cells/cm² in tissue culture flasks (BD Biosciences). Cells were expanded at 37° C. in a humidified 5% $CO_2$/95% air incubator and media was changed twice a week. After approximately 4-7 days, sub-confluent passage cells were washed with phosphate-buffered saline (PBS; GIBCO, USA), detached using 0.25% trypsin/EDTA (Gibco, Canada), counted by trypan blue exclusion in a haemocytometer and plated in a tissue culture flask at 3,000 cells/cm². The cells were passaged until there were a sufficient number of cells, after which the cells harvested to form cell encapsulated microspheres. All HFF used for this study was between passages 24 and 28 and SKOV3s were between passage 44 and 48.

Qtracker cell labelling kit (Life technologies, USA) was used to track cells in a co-culture environment. HFF were labelled with Qtracker 655 and the SKOV3s with Qtracker 800. To label the cells with Qtracker, cells were concentrated to $10^7$ cells/ml by centrifugation at 700 g for 5 minutes and resuspended in media. A 10 nM labelling solution was prepared by mixing 1 μL of the Qtracker Component A and 1 μL of the Qtracker Component B in a 1.5 ml microcentrifuge tube and incubated at room temperature for 5 minutes. 0.2 ml of DMEM was added to the mixture and vortexed for 30 seconds. $10^6$ cells at a concentration $10^7$ cells/ml was added to the labelling mixture and incubated for 60 minutes. The cells were subsequently washed twice with media and re-suspended in media for use.

Non-labelled cells were used to form SKOV3 microspheres and Fibroblasts microspheres. Labelled SKOV3s and HFF were mixed so that the ratio of SKOV3s in the mixture was 75% and were used to form the co-culture microspheres. Dried sterile Gel-MA (10 wt %) was dissolved in PBS at 37° C. and left to cool overnight at RT. A cell pellet was formed by centrifuging the cells at 0.7 rcf and the supernatant was discarded. The cell pellet was then dissolved in 10% wt Gel-MA macromer solution containing sterile filtered initiators (0.2 mM ruthenium (Ru; Sigma-Aldrich, USA) and 2 mM sodium persulfate (SPS; Sigma-Aldrich, USA)) to give a final concentration of $10 \times 10^6$ cells/ml. The solution containing the cells was into a syringe. Food grade sunflower oil was used as the continuous phase and the Gel-MA solution containing the photoinitiator and cells made up the dispersed phase. For the continuous oil phase the flow rate was set to 1 ml/minute and the dispersed gel phase it was set to 40 μl/min. The formed microspheres were then irradiated under visible light (OmniCure® S1500, Excelitas Technologies). The light was irradiated through a light filter (Rosco IR/UV filter) where only light of the wavelength 400-450 nm and final intensity of 100 mW/cm$^2$ was allowed to pass through. The formed microspheres were collected in polypropylene (Falcon) centrifuge tubes containing PBS. To separate the oil from the microspheres, the centrifuge tube was centrifuged at 0.1 g for 5 minutes. The oil was then aspirated and the pellet of spheres in PBS collected using a pasture pipette and then suspended in fresh PBS and the washing step was repeated. Each cell encapsulated microspheres was then transferred to well in a 96-well polystyrene plate (Falcon). 150 μL of cell culture media was then pipetted into the wells and placed in the incubator and the media was changed twice a week.

The DNA in the microsphere hydrogels were quantified using a CyQUANT kit (Molecular Probes) for Day 0, 7 and 12 samples. Briefly, post proteinase-K digestion, the cells in the sample were lysed and the RNA was degraded by using the provided lysis buffer with RNase A (1.35 KU/ml) added for an hour in room temperature. Samples were pipetted into a 96-well white polypropylene plate (Nunc) and GR-dye solution was added. The plate was then incubated at room temperature for 15 minutes and fluorescence was measured (Fluostar Galaxy BMG Labtechnology). A standard curve was constructed using the A-DNA provided in the kit.

TABLE 1

Cells per microsphere after fabrication (day 0).

| Cells | SKOV3 | Fibroblast | Co-culture | Theoretical |
|---|---|---|---|---|
| Cells per microsphere | 5828.63 ± 263.31 | 6168.01 ± 158.77 | 5609.71 ± 540.06 | 5235.99 |
| Coefficient of variation | 0.045 | 0.025 | 0.096 | — |

[a]n = 3
[b]No significant difference (p > 0.05) between microspheres of different cell types and the theoretical value.
[c]Theoretical value is the calculated number of cells for a microsphere of 1 mm diameter formed with a macromer containing a cell seeding density of $10 \times 10^6$ cells/ml.

After fabricating the microspheres, the number of cells per microsphere was determined. The determined value of cells per microsphere was comparable to the expected or theoretical value. The coefficient of variation shows that the variation in the cells per microsphere was low. There was also no significant difference (p>0.05) in the cells per microsphere for SKOV3, fibroblast or co-culture encapsulated microspheres and the theoretical value.

Figure 24:
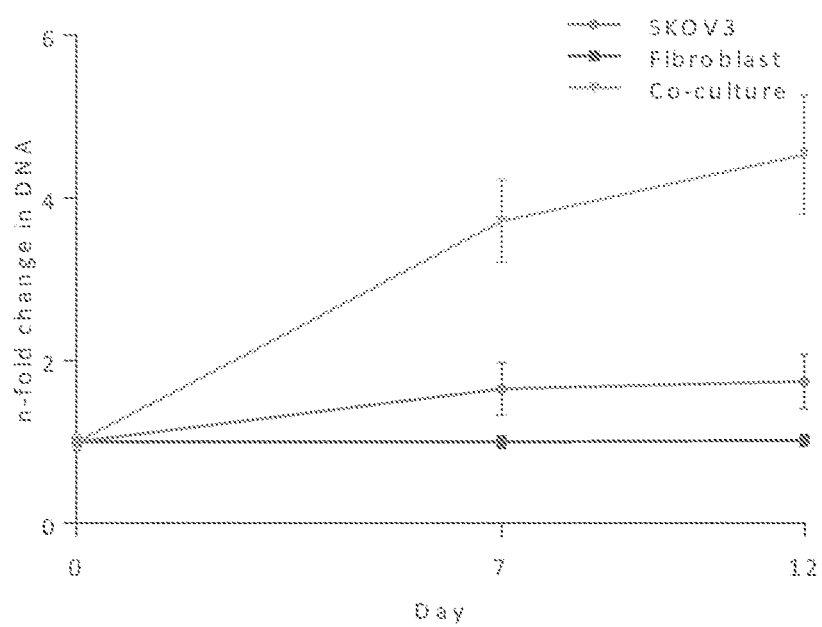
FIG. 24 shows n-fold change in DNA content (n=3) for SKOV3, fibroblast and co-culture microspheres measured on day 0, 7 and 12.
Figure 25:
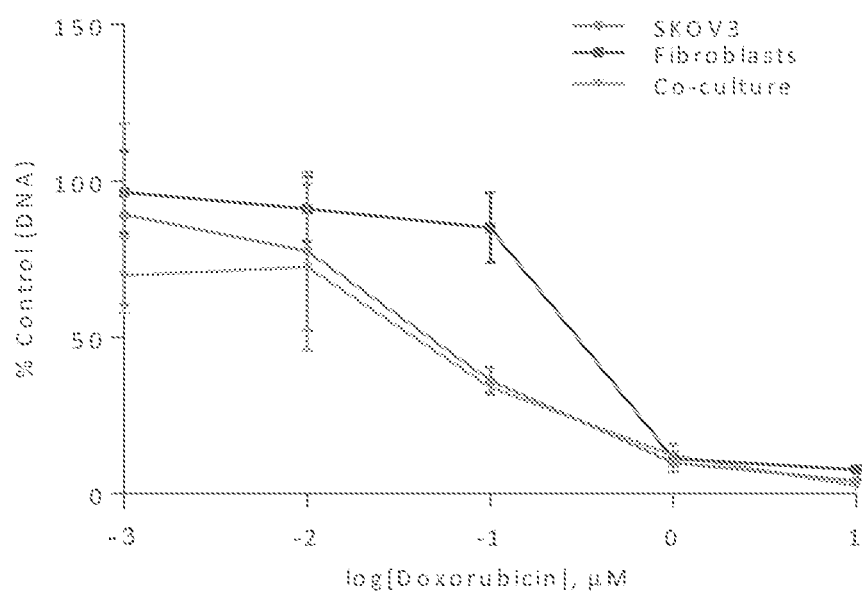
FIG. 25 shows doxorubicin dose dependent DNA content expressed in percentage control for SKOV3, fibroblast and co-culture microspheres measured after 4 days of exposure to the drug.
Figure 26:
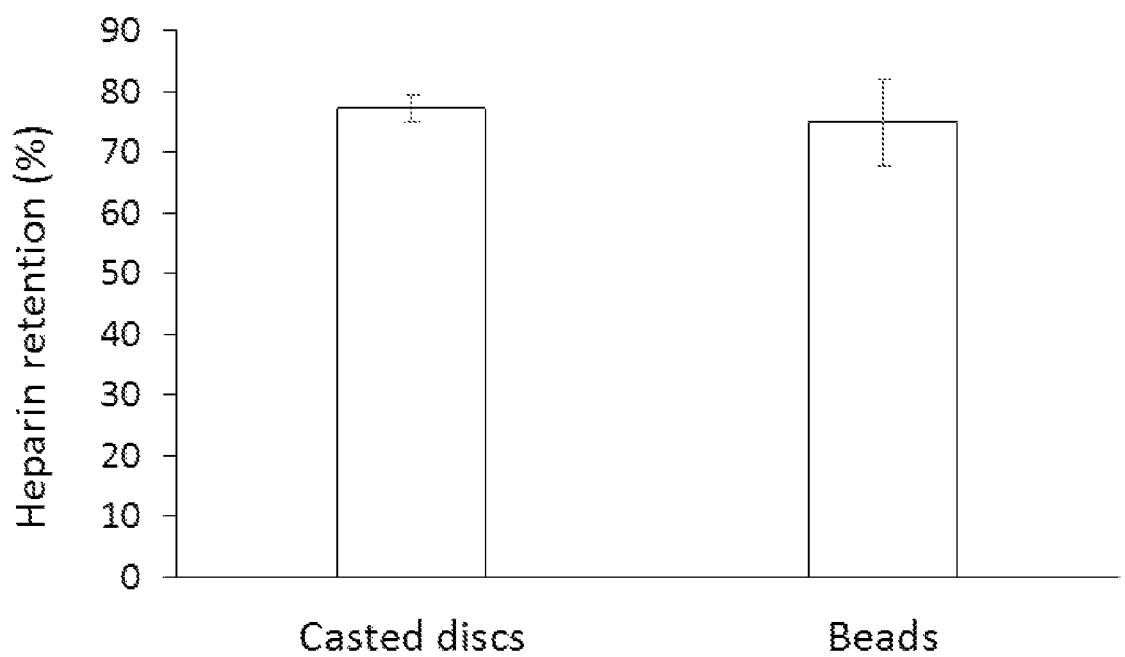
FIG. 26 shows retention of heparin-MA in gel-MA hydrogels discs or beads fabricated using the visible light system.

The n-fold change in DNA content for SKOV3, fibroblasts and co-culture microspheres culture up to day 12 is shown in FIG. 24. For the SKOV3 microspheres there was a slightly significant increase in DNA (p=0.055) between day 0 and 7, but no significant increase (p>0.05) in DNA between day 7 and 12. But with the fibroblast microspheres no significant increase or decrease (p<0.05) in DNA was observed over time. However with the co-culture microspheres, an increase in DNA content (p<0.05) from day 0 to day 7 to day 12 was observed.

Example 25: Fabrication of 3D Plotted Scaffold

A porous scaffold with a dimension of 25×25×1.8 mm was 3D plotted using a BioScaffolder (SYS+ENG, Germany). Fibres were oriented in a repeating 0-90°-90°-00 pattern in order to provide space for micro-tissue incorporation. During the fabrication process the following print parameters were set: (i) fibre spacing of 1 mm in both x and y direction, (ii) fibre height offset of 0.22 mm, (iii) print head reservoir containing the polymer heated to a temperature of 2000 and pressurised to 5 Bar, (iv) an auger speed of 63 RPM and (v) print head fitted with a 25 gauge nozzle moving with a traverse speed of 500 mm/min.

Example 26: Automated Tissue Assembly with Cancer Microspheres

The automated assembly of a construct with cancer microspheres was demonstrated by printing a scaffold using the high-temperature print head containing Polyactive 300PEGT55PBT45 and then inserting the cell (75% SKOV3s and 25% HFFs) encapsulated microspheres using the microsphere injection head. To print the assembled construct (n=3) a layer-by-layer approach was opted so as to not limit the height of the scaffold that can be constructed using the system. In this scheme the first layer of the scaffold (8 layers of fibre strands) was printed (as described earlier) and then 4 (2×2 fashion) live microspheres were inserted into the pores of the 3D plotted scaffold. This process was repeated to generate a second layer of the scaffold (4 layers of fibre strands) and then 4 more microspheres were inserted into the scaffold. But for the manually assembled scaffold, the whole scaffold was printed at once and the micro-tissues were inserted manually into pre-printed scaffolds in a similar format to the ones assembled with the automated system.

For the live/dead assay, the samples were incubated at 37° C. in 0.5 ml of Dulbecco's phosphate-buffered saline (D-PBS; Invitrogen) with 1 μM Calcein AM (Molecular Probes) for 15 minutes, then 1.5 μM Propidium Iodide (Molecular Probes) was added and incubated for 10 more minutes. After this the samples were washed twice with D-PBS and a z-stack of the sample was imaged using the Zeiss Axioimager Z1 microscope.

For the AlamarBlue assay, AlamarBlue (Invitrogen, USA) was added to the media so that the final concentration was 10% (v/v) and the samples were incubated at 37° C. for 20 hours. The reduction in AlamarBlue reagent was calculated colorimetrically using the equations provided by the manufacturer after measuring the absorbance at 570 nm, using 600 nm as a reference wavelength (Fluostar Galaxy BMG Labtechnology).

Co-culture microspheres were assembled by the automated system via the layer-by-layer approach and was compared for viability with the manually assembled construct. Visual inspection of the live/dead fluorescence microscopy images of the manually assembled construct and the construct assembled using the assembly system showed no obvious differences. The results from the alamarBlue assay supported this as there was no significant difference (p>0.05) in percentage of AlamarBlue reduced between the manually assembled construct and the construct assembled using the automated assembly system.

Example 27: Cytotoxic Test

The cytotoxicity test was used to evaluate in vitro antitumor activity of Doxorubicin on cells in 2D, microspheres and assembled cancer construct. Doxorubicin was dissolved in DMSO so that the maximum final concentration of DMSO in media did not exceed 0.5% v/v of DMSO. On Day 0, fabricated SKOV3, HFF and co-culture micro-tissues were transferred to a 96-well plate and 150 µl of media per well was added. On day 1 of forming the microspheres, SKOV3, HFF and co-culture cancer constructs were manually assembled and transferred to a 24-well plate with 1.2 ml of media per well. On day 7, for the cytotoxicity test on 2D model, SKOV3s, HFFs and co-culture (75% SKOV3 and 25% HFF) cells were seeded onto a 48-well plate at 30,000 cells and 200 µl of media per well. The next day (day 8), all samples were treated with different concentrations of Doxorubicin—no drug control, 0.001 µM, 0.01 µM, 0.1 µM, 1 µM, 10 µM. Media with 5% FBS containing the specific concentration of drug was changed every 2 days. After 4 days of exposure to the drug, AlamarBlue assay was conducted to measure metabolic activity of cells of the samples. For the AlamarBlue assay, all samples were transferred to a fresh well plate, AlamarBlue (Invitrogen, USA) was added to the media so that the final concentration was 10% (v/v) and the samples were incubated at 37° C. for 20 hours. Fluorometric measurements were made at an excitation wavelength of 545 nm and emission wavelength of 590 nm.

The general trend observed for all cell types was that the $IC_{50}$ values (Table 2) for the drug was the lowest for the cells in 2D, slightly higher for the microspheres (1-4 fold increase compared to cells in 2D) and highest for the assembled constructs (48-70 fold increase compared to cells in 2D). SKOV3s had the lowest $IC_{50}$ value in all models. The co-culture micro-spheres and assembled constructs had a higher $IC_{50}$ value compared to the SKOV3 or HFF only micro-spheres and assembled constructs. However, for cells in 2D, HFF had the highest $IC_{50}$ value.

The DNA content expressed in percentage of control against drug concentration for microspheres is shown in FIG. 5. The trend of decreasing DNA content with increasing drug concentration is similar to the dose-response curve. SKOV3 and co-culture microspheres show a similar trend, but fibroblasts microspheres show a slight lag in the reduction of DNA content compared to SKOV3 and co-culture microspheres. Darkfield images of the cancer construct revealed that at higher concentration of drug there was an atrophy of the tissue present in construct which was especially noticeable at 1 µM concentration of the drug and at 10 µM there was almost no tissue present within the construct.

TABLE 2

Cytotoxicity of doxorubicin

| | IC50 (µM) | | | Fold change in IC50 | | |
|---|---|---|---|---|---|---|
| Cells | 2D | Microspheres | Assembled construct | Microspheres/ monolayer | Assembled construct/ microspheres | Assembled construct/ monolayer |
| SKOV3 | 0.05 | 0.15 | 2.41 | 2.96 | 16.33 | 48.32 |
| Fibroblast | 0.16 | 0.18 | 3.81 | 1.14 | 21.41 | 24.32 |
| Co-culture | 0.08 | 0.29 | 5.56 | 3.63 | 19.34 | 70.14 |

Example 28: Synthesis of Heparin-Methacryloyl (Hep-MA)

Methacrylated heparin (Hep-MA) was synthesised using the protocol of Example 1. Briefly, heparin was dissolved in PBS at 10% and 1% and allowed to react with MAAh, with 20- and 10-fold molar excess over hydroxyl groups, correspondingly. The reaction was kept at 4° C. under continuous stirring and repeatedly adjusting the pH to 8 during 24 h. The reaction solution was dialysed (MWCO 14,000 Da) against deionised water in order to remove unreacted molecules. The functionalised polymer was sterile filtered and lyophilised followed by storage at −20° C. until use.

Example 29: Incorporation of Hep-MA into Gel-MA Hydrogels

Hydrogel precursor solution (9.5 wt % Gel-MA+0.5 wt % Hep-MA) was prepared using PBS, supplemented with a final concentration of 0.2/2 mM Ru/SPS, injected into a custom-built Teflon mould that was covered by a glass slide for minimized oxygen inhibition effects, and irradiated with 400-450 nm visible light at an intensity of 3 mW/cm2 for 15 min. All fabricated hydrogels had initial dimensions of approximately 06×2 mm. Alternatively, Gel-MA/Hep-MA hydrogel beads were fabricated using a microfluidic device consisted of PTFE tubing, T-junctions and a fused silica capillary. The continuous phase was sunflower oil where the dispersed phase was a 9.5 wt % Gel-MA+0.5 wt % Hep-MA+0.2/2 Ru/SPS (mM). The oil and hydrogel precursor solution were pumped through the device at a rate of 1 ml/min and 50 µl/min respectively. The hydrogel beads were sheared off by the oil and subjected to 100 mW/cm$^2$ of visible light for crosslinking. The overall exposure time was kept to 3 minutes.

Example 30: Quantification of Macromer Retention in Cell Free Hydrogels

Four hydrogel compositions were polymerised and incubated in PBS, containing 0.1% sodium azide, at 37° C. for up to 14 days. At each time point, samples were removed from PBS and digested at 56° C. in 1 mg/ml proteinase K, dissolved in 10 mM Tris-HCl and 1 mM disodium EDTA solution, and stored at −20° C. along with corresponding liquid solution until analysis. Samples were allowed to react with DMMB to quantify heparin content. In brief, 50 μl of each digested gel sample, corresponding PBS liquid, and standard curve dilutions were transferred in triplicates to a 96-well micro plate, to which 200 μl of DMMB solution was added and the absorbance was read twice at 535 nm (Thermo Scientific Varioskan Flash). Heparin content in both hydrogels and surrounding liquid could be calculated from a matching standard curve generated by reacting known amounts of heparin and HepMA, with the DMMB agent. The retention, defined as the percentage of macromer not released to the surrounding liquid, could then be calculated for each time point using the following equation:

$$\text{Macromer retention (\%)} = \frac{m_g}{(m_g + m_l)} \times 100\%$$

where $m_g$ is the mass of heparin macromers found in the digested hydrogels and $m_l$ is the mass of heparin macromers found leached out to the surrounding PBS that the corresponding hydrogel was submerged in.

Example 31: Incorporation of MgCO₃ Nanoparticles into Gel-MA Hydrogels $MgCO_3$ nanostructures (n$MgCO_3$) were synthesised by a precipitation reaction between magnesium chloride and sodium carbonate. As-prepared nanostructures were washed, centrifuged and dried. 5 wt % Gel-MA hydrogels were fabricated with (0.5 mg/ml or 1.5 mg/ml) and without $MgCO_3$ nanostructures, in the presence of 0.2/2 mM Ru/SPS and irradiated with 30 mW/cm² of visible light for 10 minutes.

Example 32: Encapsulation of MSCs in Gel-MA/MgCO₃ Hydrogels

Human bone marrow derived mesenchymal stromal cells (MSCs) were encapsulated into the Gel-MA/$MgCO_3$ hydrogels at a density of 5×10⁶ cells/ml. Samples were cultured in osteogenic differentiation media (α–MEM+FBS+dexamethasone+β-glycerophosphate+ascorbic acid) for up to 28 days.

Example 33: Synthesis of Gelatin-Norbornene (Gel-NOR) Hydrogels

Gelatin was dissolved in phosphate buffered saline (PBS) in a round bottom flask at 10 wt % and 50° C. Carbic anhydride (CA) was added to the gelatin solution to make up to a final concentration of 20 wt % and allowed to stir at 50° C. 1M sodium hydroxide solution was added dropwise to the reaction solution to facilitate CA dissolution. Once all the CA was dissolved, the pH was adjusted to 7.7-8. Reaction was allowed to continue for 24 hours. After the reaction was complete, the solution was diluted 3 times with warm PBS, then centrifuged for 3 minutes at 4000 rpm to remove all the unreacted CA. The supernatant was then dialysed against $H_2O$ at 50° C. for 3 days, with the water changed regularly, sterile filtered through a 0.22 μm filter, followed by freeze-drying to obtain dried sterile Gel-NOR macromer. A fluoraldehyde assay was used to quantify the degree of functionalisation of the Gel-NOR.

Gel-NOR hydrogels were prepared in PBS at various weight percentages (2.5, 5, 10 wt %), and then mixed with different thiolated molecules (DTT, PEG4SH and PEG8SH) to achieve functional group ratios of NOR:SH (1:1, 1:2, 1:3, 1:6 and 1:12). After the addition of the photoinitiator (1/10 mM RU/SPS), the hydrogel precursor solutions were photopolymerised with 30 mW/cm² of Vis light (Rosco IR/UV filter equipped to OmniCure® 51500, Excelitas Technologies) for 3 min. Cylindrical constructs (h=2 mm, 0=6 mm) were prepared using custom-built molds. After polymerisation, each hydrogel was weighed and three samples per hydrogel composition were directly lyophilised to record their initial dry weights and determine the actual macromer weight fraction, the initial dry weight of the remaining samples, the mass loss and mass swelling ratio (q), and the sol fraction (using the same methodology as Example 16).

Figure 29:
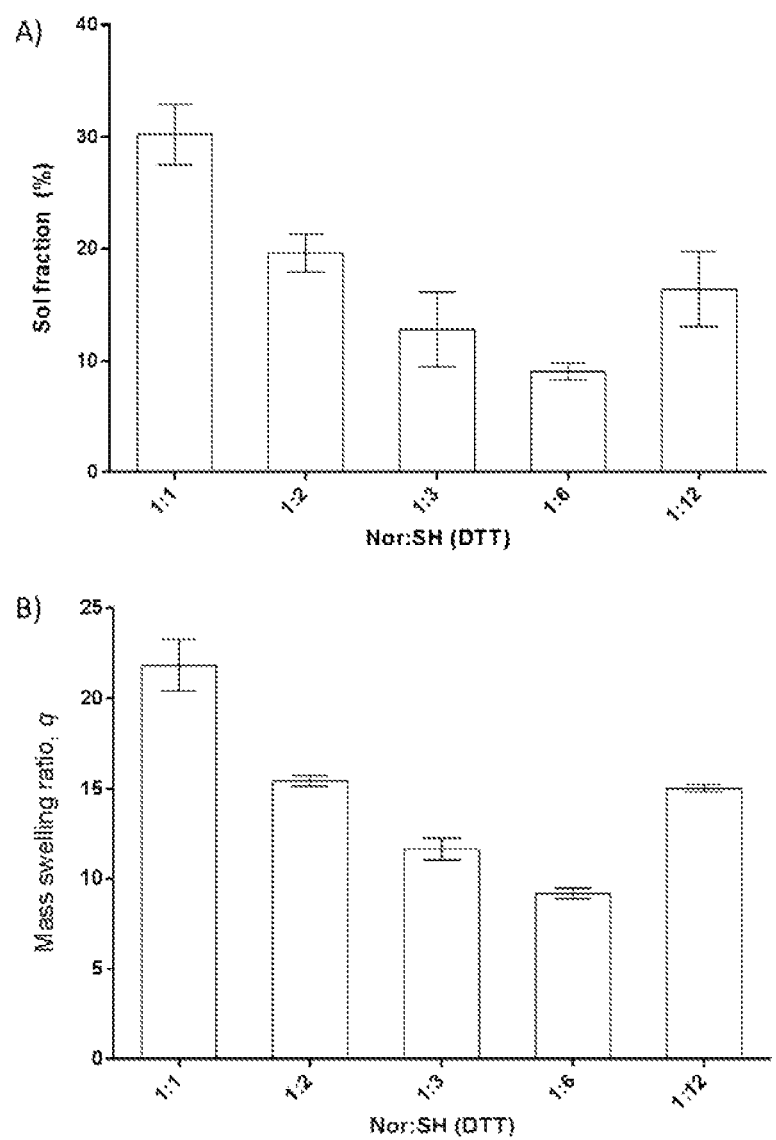
FIG. 29 shows sol fraction and mass swelling ratio of Gel-NOR hydrogels fabricated using various NOR:SH ratios. Irradiation conditions were kept at 1/10 (mM/mM), 30 mW/cm$^2$ and 3 minutes.

Gel-NOR hydrogels of good crosslinking efficiency (sol fraction <20%) were successfully fabricated at a NOR:SH ratio higher than 1:2 using DTT (FIG. 29). This result proved that the visible light initiators are compatible with the thiol-norbornene step-growth polymerisation. It was also observed that the mass swelling ratio decreases in conjunction with the decrease in sol fraction values.

Figure 30:
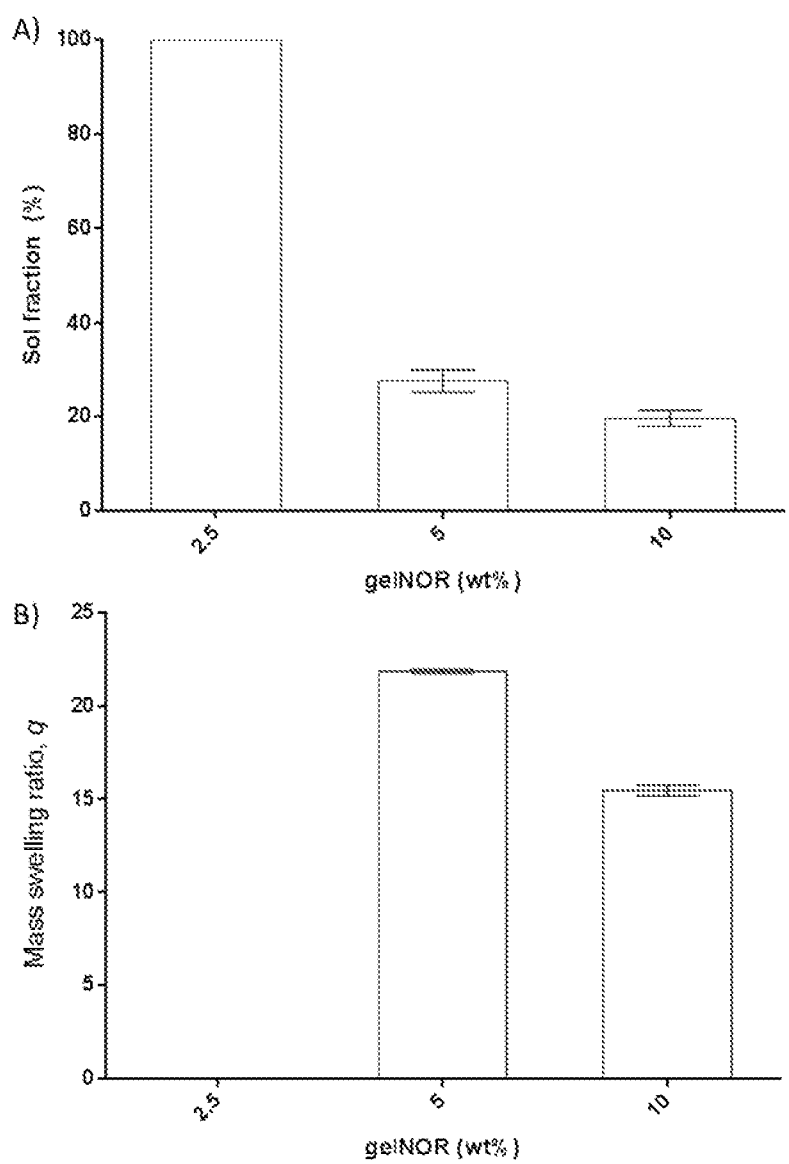
FIG. 30 shows sol fraction and mass swelling ratio of Gel-NOR hydrogels (2.5, 5 and 10 wt %) fabricated using 1:2 NOR:SH ratios and DTT. Irradiation conditions were kept at 1/10 (mM/mM), 30 mW/cm$^2$ and 3 minutes.

Using DTT (MW=154.23 Da) and keeping the NOR:SH ratio constant at 1:2, 5 wt % Gel-NOR gels were successfully fabricated with comparable sol fraction to the 10 wt % gel, indicating good crosslinking efficiency (FIG. 30). Reducing the macromer concentration also increased the mass swelling ratio significantly, which is in accordance to results previously reported in the literature. However, no gels were able to be formed at 2.5 wt %.

Figure 31:
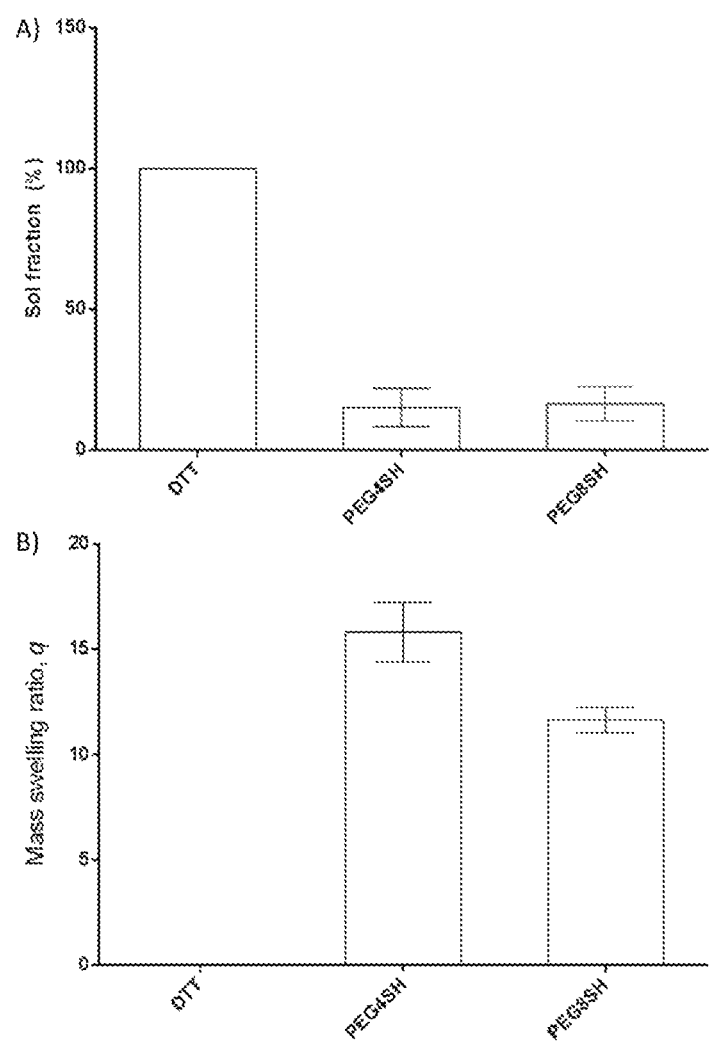
FIG. 31 shows sol fraction and mass swelling ratio of 2.5 wt % Gel-NOR hydrogels fabricated using 1:2 NOR:SH ratios. Different thiolated molecules (DTT, PEG4SH and PEG8SH) were used as the crosslinker. Irradiation conditions were kept at 1/10 (mM/mM), 30 mW/cm$^2$ and 3 minutes.

However, when using thiolated molecules of much larger molecular weight (PEG4SH and PEG8SH, both MW=10 kDa), 2.5 wt % Gel-NOR hydrogels were successfully fabricated using a similar ratio of 1:2 NOR:SH (FIG. 31). This result was not unexpected as larger thiolated molecules increase the accessibility of the NOR groups grafted on gelatin, allowing easier step-growth polymerisation between the NOR and thiol groups.

Example 34: Cell Encapsulation in Gel-NOR Hydrogels

Human umbilical vein endothelial cells (HUVEC) and human mesenchymal stromal cells (MSC) were encapsulated in 5 wt % Gel-NOR hydrogels, using DTT as the crosslinker at 1:2 (NOR:SH) ratio. The cell density of HUVEC:MSC was kept at 4:1 ratio, with 4×10⁶ HUVEC/ml and 1×10⁶ MSC/ml density. Gel-NOR laden hydrogels were cultured in vascular cell basal medium purchased from ATCC, supplemented with 5 ng/ml vascular endothelial growth factor (VEGF), 5 ng/ml epidermal growth factor (EGF), 5 ng/ml fibroblast growth factor (FGF), 15 ng/ml insulin-like growth factor (IGF-1), 10 mM L-glutamine, 0.75 units/ml heparin sulfate, 1 μg/ml hydrocortisone, 50 μg/ml ascorbic acid and 2 w/v % fetal bovine serum. Samples were cultured for 14 days then fixed in 4% paraformaldehyde and immuno-stained for platelet endothelial cell adhesion molecule (PECAM-1) and F-actin.

Figure 32:
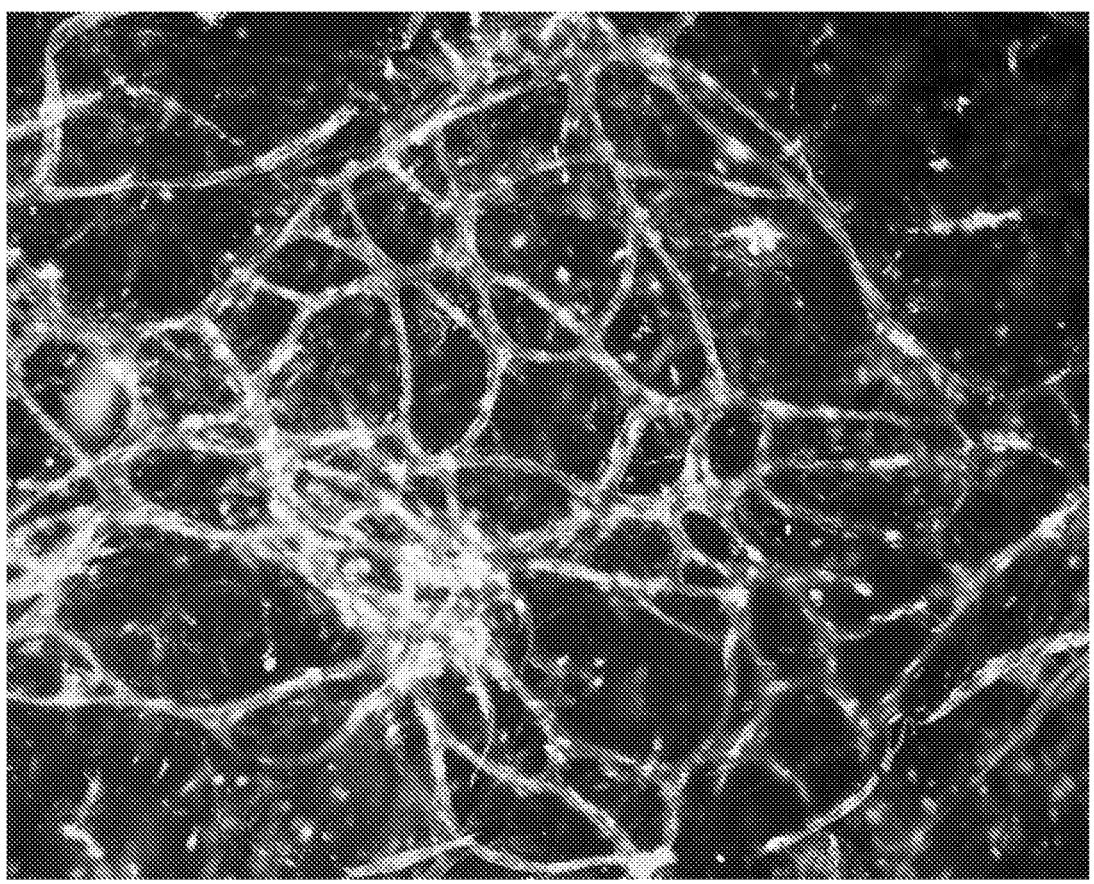
FIG. 32 shows vasculogenesis in 5 wt % Gel-NOR hydrogels, crosslinked with 1:2 NOR:SH (DTT), 1/10 mM Ru/SPS, 30 mW/cm$^2$ for 3 minutes. Samples were cultured for 14 days.

HUVEC and MSC were successfully encapsulated in the Gel-NOR hydrogels with good survival and metabolic activity. The vasculogenesis functionality of the HUVEC cells was assessed by the formation of vasculature networks within the hydrogels after 14 days of culture. FIG. 32 shows tubular networks formed by the HUVEC as stained positive by PECAM, and co-localisation of MSC around the tubular structures to stabilise the formed networks. This result shows that Gel-NOR hydrogels can be used for soft tissue engineering, such as prevascularisation of bone scaffolds.

Although the invention has been described by way of example, it should be appreciated that variations and modifications may be made without departing from the scope of the invention as defined in the claims. Furthermore, where known equivalents exist to specific features, such equivalents are incorporated as if specifically referred in this specification.

The invention claimed is:

1. A method for preparing a hydrogel comprising:
   (i) mixing a solution of polymer with a photoinitiator, where the polymer comprises multiple subunits each having a non-aromatic unsaturated functional group that comprises a carbon-carbon double bond; and
   (ii) irradiating the mixture with visible light to produce the hydrogel; wherein the photoinitiator comprises a ruthenium(II) compound and sodium persulfate, ammonium persulfate, or potassium persulfate.

2. The method as claimed in claim 1, wherein the unsaturated functional group is selected from the group consisting of methacrylate, acrylate, methacrylamide, acrylamide, norbornene, propiolate, and allyl.

3. The method as claimed in claim 1, wherein the hydrogel forms by cross-linking of unsaturated functional groups by a chain-growth polymerisation process or by a step-growth polymerisation process.

4. The method as claimed in claim 3, wherein the step-growth polymerisation process comprises a reaction between one or more unsaturated functional groups of one polymer chain and thiolated functional groups of another polymer chain.

5. The method as claimed in claim 1, wherein the ruthenium(II) compound is tris(2,2-bipyridyl)dichlororuthenium (II) hexahydrate.

6. The method as claimed in claim 1, wherein the polymer is a synthetic polymer.

7. The method as claimed in claim 6, wherein the synthetic polymer is selected from the group consisting of polyvinyl alcohol (PVA), polyethylene glycol (PEG), poly(2-hydroxyethyl methacrylate) (pHEMA), poly(acrylamide), poly(methacrylamide), poly(methyl methacrylate) (PMMA), poly(lactide-co-trimethylene carbonate) (PTMC), polyfumarate, poly(lactic acid) (PLA), polycaprolactone (PCL) and poly(N-vinyl-2-pyrrolidone).

8. The method as claimed in claim 1, wherein the polymer is a natural polymer.

9. The method as claimed in claim 8, wherein the natural polymer is selected from the group consisting of alginate, hyaluronan, heparin, silk fibroin, silk sericin, methylcellulose, gellan gum, chondroitin sulfate, chitosan, fibrinogen, collagen, gelatin, vascular endothelial growth factor (VEGF), bone morphogenic protein (BMP), epidermal growth factor (EGF) and transforming growth factor (TGF).

10. The method as claimed in claim 1, wherein the visible light has a wavelength in the range 400-450 nm.

11. The method as claimed in claim 1, wherein the hydrogel is a gelatin-methacryloyl hydrogel, a heparin-methacryloyi hydrogel, a poly(vinyl alcohol)-methacryloyl hydrogel, a gelatin-allyloyl hydrogel, or a gelatin-norbornenyl hydrogel.

12. The method as claimed in claim 11, wherein the gelatin-methacryloyl hydrogel is prepared according to a process comprising the steps:
   (i) contacting an aqueous solution of gelatin with methacrylic anhydride to produce gelatin-methacryloyl;
   (ii) mixing the gelatin-methacryloyl with a ruthenium(II) compound and sodium persulfate; and
   (iii) irradiating the mixture with visible light to produce the hydrogel.

13. The method as claimed in claim 1, wherein the visible light has an intensity of 10-50 mW/cm2.

14. The method as claimed in claim 1, wherein the ratio of ruthenium(II) compound to sodium persulfate is approximately 1:10.

15. The method as claimed in claim 1, wherein the time for irradiating the mixture in step (iii) is 2-15 minutes.

16. The method as claimed in claim 1, wherein the hydrogel comprises encapsulated biological cells and/or cellular spheroids.

17. The method as claimed in claim 1, wherein the hydrogel comprises one or more encapsulated growth factors.

18. The method as claimed in claim 17, wherein the one or more growth factors are selected from the group comprising VEGF, BMP2, EGF, BDNF and TGF-β.

* * * * *